(12) United States Patent
Shinomiya et al.

(10) Patent No.: US 7,872,117 B2
(45) Date of Patent: Jan. 18, 2011

(54) C-MET SIRNA ADENOVIRUS VECTORS INHIBIT CANCER CELL GROWTH, INVASION AND TUMORIGENICITY

(75) Inventors: Nariyoshi Shinomiya, Saitama (JP); George F. Vande Woude, Ada, MI (US)

(73) Assignee: Van Andel Research Institute, Grand Rapids, MI (US)

( * ) Notice: Subject to any disclaimer, the term of this patent is extended or adjusted under 35 U.S.C. 154(b) by 424 days.

(21) Appl. No.: 10/599,327

(22) PCT Filed: Mar. 28, 2005

(86) PCT No.: PCT/US2005/010441

§ 371 (c)(1), (2), (4) Date: Mar. 12, 2007

(87) PCT Pub. No.: WO2005/095622

PCT Pub. Date: Oct. 13, 2005

(65) Prior Publication Data

US 2007/0232555 A1    Oct. 4, 2007

Related U.S. Application Data

(60) Provisional application No. 60/556,473, filed on Mar. 26, 2004.

(51) Int. Cl.
*C07H 21/04* (2006.01)
*C12N 15/00* (2006.01)
*A61K 31/70* (2006.01)

(52) U.S. Cl. .................. 536/24.5; 536/23.1; 435/320.1; 514/44

(58) Field of Classification Search ........................ None
See application file for complete search history.

(56) References Cited

U.S. PATENT DOCUMENTS

| | | | | |
|---|---|---|---|---|
| 5,716,832 | A | * | 2/1998 | Barber et al. ............ 435/235.1 |
| 5,795,715 | A | * | 8/1998 | Livache et al. .................. 435/6 |
| 5,932,210 | A | * | 8/1999 | Gregory et al. ............ 424/93.2 |
| 2003/0180756 | A1 | * | 9/2003 | Shi et al. ........................ 435/6 |
| 2004/0162255 | A1 | * | 8/2004 | Kaemmerer ................. 514/44 |
| 2004/0259247 | A1 | * | 12/2004 | Tuschl et al. ................ 435/375 |
| 2004/0265230 | A1 | * | 12/2004 | Martinez et al. ........... 424/1.49 |

FOREIGN PATENT DOCUMENTS

EP          1243596 A2 *   9/2002

OTHER PUBLICATIONS

Abounader et al. (2002) FASEB J. 16(1):108-110.*
Elbashir et al. et al. (2002) Methods 26:199-213.*
Good et al. (1997) "Expression of small, therapeutic RNAs in human cell nuclei" Gene Therapy 4:45-54.*
Birchmeier C, et al. Met, Metastasis, Motility and More. Nat Rev Mol Cell Biol, No. 4: 915-925 (Dec. 2003).
Cotella N, et al. Role of the MET/HGF receptor in proliferation and invasive behavior of osteosarcoma. FASEB J. vol. 17: pp. 1162-1164 (Jun. 2003).
Fire A, et al. Potent and specific genetic interference by double-stranded RNA in Caenorhabditis elegans. Nature (London) vol. 391: pp. 806-811 (Feb. 1998).
Gherardi E, et al. Hepatocyte Growth Factor-Scatter Factor: Mitogen, Motogen, and Met. Cancer Cells (Cold Spring Harbor) vol. 3: pp. 227-232 (Jun. 1991).
Herynk M, et al. Down-Regulation of c-Met Inhibits Growth in the Liver of Human Colorectal Carcinoma Cells. Cancer Research vol. 63: pp. 2990-2996 (Jun. 1, 2003).
Lin S, et al. D-RNAi (Messenger RNA-antisense DNA Interference) as a Novel Defense System Against Cancer and Viral Infections. Curr Cancer Drug Targets vol. 1: pp. 241-247 (2001).
Maemondo M, et al. Targeting Angiogenesis and HGF Function Using an Adenoviral Vector Expressing the HGF Antagonist NK4 for Cancer Therapy. Molecular Therapy vol. 5 (No. 2): pp. 177-185 (Feb. 2002).
Paddison P, et al. RNA interference: the new somatic cell genetics? Cancer Cell vol. 2: pp. 17-23 (Jul. 2002).
Rong S, et al. Tumorigenicity of the met Proto-Oncogene and the Gene for Hepatocyte Growth Factor. Mol Cell Biology vol. 12 (No. 11): pp. 5152-5158 (Nov. 1992).
Shinomiya N, et al. Suppression of Met Expression: A Possible Cancer Treatment. Clinical Cancer Research vol. 9: pp. 5085-5090 (Nov. 1, 2003).
Sui G, et al. A DNA vector-based RNAi technology to suppress gene expression in mammalian cells. Proc Natl Acad Sci vol. 99 (No. 8): pp. 5515-5520 (Apr. 16, 2002).

(Continued)

Primary Examiner—Tracy Vivlemore
(74) Attorney, Agent, or Firm—Price, Heneveld, Cooper, DeWitt & Litton, LLP

(57) ABSTRACT

Suppression of the Hepatocyte growth factor/scatter factor (HGF/SF)-Met signaling pathway by targeting the Met protein tyrosine kinase was tested as strategy for suppressing tumor growth. Using RNA interference (RNAi) technology and adenoviruses carrying siRNA (Ad Met siRNA) target sequences dramatically reduced Met expression in mouse, dog and human tumor cells. Met was suppressed using Ad Met siRNA in mouse mammary tumor (DA3) cells and Met-transformed (NIH3T3 (M114) cells as well as human prostate cancer, sarcoma, glioblastoma, gastric and ovarian cancer cells. Furthermore, the Ad Met siRNA infection reversed transformed cell morphology. Ad Met siRNA killed cancer cells by inducing apoptosis. RNAi targeting Met suppressed HGF/SF-mediated scattering as well as ligand-mediated invasion activity and growth of tumor cells. Met siRNA infection also abrogated downstream Met signaling to molecules such as Akt and p44/42 MAPK. Importantly, the Met siRNA triggered apoptosis was correlated to suppressed tumorigenicity in vivo. Intro-tumoral infection with c-met siRNA adenovirus vectors produced significant reduction in tumor growth. Thus Met RNAi is an effective weapon for targeting Met expression and for treating c-Met[+] cancers.

24 Claims, 11 Drawing Sheets

OTHER PUBLICATIONS

Tuschl T, et al. Targeted mRNA degradation by double-stranded RNA in vitro. Genes & Development vol. 13: pp. 3191-3197 (Oct. 1999).

Abounader, Roger et al., "In vivo targeting of SF/HGF and c-met expression via U1snRNA/ribozymes inhibits glioma growth and angiogenesis and promotes apoptosis," The FASEB Journal, vol. 16, Jan. 2002, pp. 108-110.

Ma, Patrick C. et al., "c-Met: Structure, functions and potential for therapeutic inhibition," Cancer and Metastasis Reviews, vol. 22, Dec. 2003, pp. 309-325.

Shinomiya, Nariyoshi et al., "RNA interference reveals that ligand-independent met activity is required for tumor cell signaling and survival," Cancer Research, vol. 64, Nov. 1, 2004, pp. 7962-7970.

* cited by examiner

Fig. 1A  M114 cells

Fig. 1B  DBTRG human glioblastoma cells

Fig. 1C  PC-3 human prostate cancer cells

Fig. 1D  MKN45 human gastric cancer cells

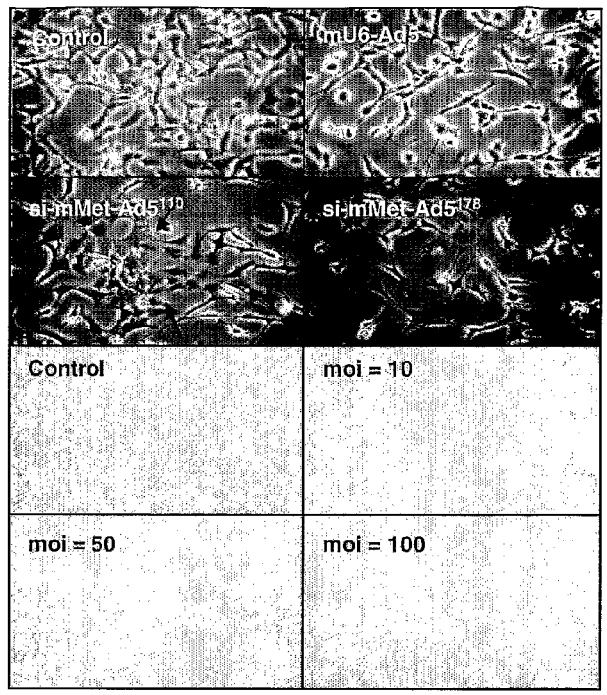
Fig. 2A  M114 cells
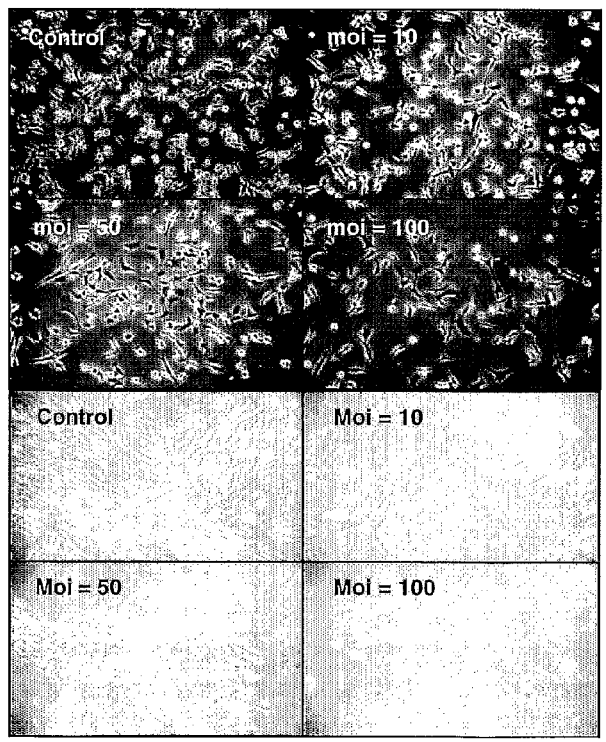
Fig. 2B  DBTRG cells

C-MET SIRNA ADENOVIRUS VECTORS INHIBIT CANCER CELL GROWTH, INVASION AND TUMORIGENICITY

CROSS-REFERENCE TO RELATED APPLICATION

This application is a national stage entry of PCT/US05/10441 filed Mar. 28, 2005 and claims priority to U.S. Provisional Patent Application No. 60/556,473 filed on Mar. 26, 2004.

BACKGROUND OF THE INVENTION

1. Field of the Invention

The present invention in the field of molecular biology and medicine relates to interfering RNA (RNAi) compositions and methods of using them to reduce the expression of the Met oncogene, a receptor for hepatocyte growth factor/scatter factor (HGF/SF), in tumor cells. This promotes apoptosis and results in inhibition of tumor cell growth, invasion and metastasis.

2. Description of the Background Art

Hepatocyte growth factor/scatter factor (HGF/SF) is a pleiotropic factor that induces a wide range of cellular functions, including proliferation, migration, angiogenesis and morphogenesis (Gherardi, E et al., *Cancer Cells* 3:227-232, 1991; Takebayashi, T et al., *J Cell Biol* 129:1411-1419, 1995; Jeffers, M et al., *Cell Growth Differ* 7:1805-1813, 1996; Sonnenberg, E et al., *J Cell Biol* 123:223-235, 1993) Met, the only known receptor for the HGF/SF ligand, can mediate signaling to downstream molecules (Birchmeier, C et al. *Trends Cell Biol* 8:404-410, 1998; Stewart, F *Rev Reprod* 1:144-148, 1996; Furge, K A et al., *Oncogene* 19:5582-5589, 2000; Birchmeier, C et al., *Nat Rev Mol Cell Biol* 4:915-925, 2003; Bottaro, D et al., *Science* 251:802-804, 1991).

HGF/SF is produced mainly by mesenchymal cells, while Met is preferentially expressed in epithelial and endothelial cells (Jeffers, M et al., Oncogene 13:853-856, 1996; Yang, X M et al., *Lab Invest* 73:483-491, 1995; Sonnenberg, E et al., *Exs* 65:381-394, 1993). In many types of tumor cells, Met signaling is activated through ligand-dependent autocrine or paracrine mechanisms (Park, W S et al., *Apmis* 108:195-200, 2000; Morello, S et seq., *J Cell Physiol* 189:285-290, 2001). Enhanced signal transduction via the stimulation of this receptor contributes to the malignant phenotype. Activating mutations in the Met receptor, first discovered in human papillary renal carcinomas (Schmidt, L et al., *Nat Genet* 16:68-73, 1997) have now been discovered in several different types of cancers and metastatic lesions. In mouse models, these mutations induce transformation, proliferation and invasion in vitro, as well as tumorigenicity and metastasis in vivo (Jeffers, M et al., *Oncogene* 17:2691-2700, 1998; Jeffers, M et al., *Proc Natl Acad Sci* USA 94:11445-11450, 1997)

HGF/SF binding to Met activates signaling downstream (Ponzetto, C et al., *Cell* 77:261-271, 1994) through various pathways such as the Ras mitogen-activated protein kinase (MAPK) pathways through Grb2-SOS complex formation (Ponzetto, C et al, *J Biol Chem* 271:14119-14123, 1996) or the Ras and Rac pathways (Ridley, A J et al., *Mol Cell Biol* 15:1110-1122, 1995) responsible for tubulo-morphogenesis (Sachs, M et al., *J Cell Biol* 133:1095-1107, 1996) and cell spreading/actin reorganization. Likewise, the STAT pathway, particularly STAT3 activation, is required for HGF/SF-Met-mediated growth in soft agar (Zhang, Y W et al., *Oncogene* 21:217-226, 2002), and PI3 kinase activation followed by Akt phosphorylation contributes to the prevention of apoptotic cell death (Xiao, G H et al., *Proc Natl Acad Sci USA* 98:247-252, 2001; Fan, S et al., *Mol Cell Biol* 21:4968-4984, 2001). In addition, HGF/SF-Met signaling can up-regulate the production of matrix metalloproteinases and urokinase that induce the degradation of extracellular matrices and basement membrane and enhance tumor invasion and metastasis (Harvey, P et al., *Br J Cancer* 83:1147-1153, 2000; Kermorgant, S et al., *Carcinogenesis* 22:1035-1042, 2001). Moreover, the activation of Met protein (Jeffers et al., 1997, supra) is involved in the induction of blood vessel formation in tumors by increasing the production of VEGF (Rosen, E M et al., *Ciba Found Symp* 212:215-226, 227-229, 1997; Tomita, N et al., *Circulation* 107:1411-1417, 2003) and by simultaneously shutting off the anti-angiogenesis factor thrombospondin-1 (Zhang, Y W et al., *Proc Natl Acad Sci USA* in press 2003; U.S. Ser. No. 60/484,676).

Since HGF/SF-Met signaling is implicated in a wide range of tumors and regulates biological activities that contribute to the tumor cell malignancy, targeting the Met receptor has become a subject of interest in the field of cancer biology (Birchmeier et al., supra). Cao et al. (Cao, B et al., *Proc Natl Acad Sci USA* 98:7443-7448, 2001) showed that HGF/SF-neutralizing antibodies efficiently block in vitro scattering and branching morphogenesis and can suppress the in vivo growth of HGF/SF-Met signal-dependent glioblastoma cell xenografts in nude mice. This suggests that interrupting the autocrine and/or paracrine HGF/SF-Met signaling in tumors that depend on this pathway is a potential intervention strategy.

The administration of c-met-antisense oligonucleotides is another molecular approach used to block Met function in cancer cells. A recent report showed that (a) c-met-antisense oligonucleotides decreased Met protein levels in the LoVo human colon cancer cell line and (b) apoptotic cell death (induced by serum deprivation) was more prominent in antisense-treated cells than in controls (Kitamura, S et al., *Br J Cancer* 83:668-673, 2000).

Production of the dominant negative ("DN") forms of the Met protein is another approach to suppressing Met function. DN-Met in DA3 mouse mammary adenocarcinoma cells reduces tumorigenicity in vivo and metastatic potential (Firon, M et al., *Oncogene* 19:2386-2397, 2000). By using DN-Met that has inactivating mutations at both ATP binding sites in the kinase domain and at two important Tyr residues in the multidocking site, Furge et al. showed that inhibition of the Met receptor can suppress Ras-mediated metastasis (Furge, K A et al., *Proc Natl Acad Sci USA* 98:10722-10727, 2001). Ribozymes that target Met mRNA constitute a more direct approach to suppressing Met expression. Abounader et al. designed a hammerhead ribozyme against Met and showed that reduction of Met expression by the ribozyme suppressed anchorage-independent in vitro colony formation and in vivo tumorigenicity (Abounader, R et al., *J Natl Cancer Inst* 91:1548-1556, 1999. These investigators also showed that Met targeting by the ribozyme suppressed tumor growth and angiogenesis and, in turn, promoted apoptotic cell death (Abounader, R et al., *Faseb J* 16: 108-110, 2002). Christensen et al. disclosed that selective inhibition of Met tyrosine kinase activity using ATP-competitive small molecules had anti-tumor effects and thus anti-cancer therapeutic potential (Christensen, J G et al., *Canc Res* 63:7345-7355, 2003).

RNA interference (RNAi) is a recently reported phenomenon that has developed into a new approach for elucidating gene function. RNAi is a sequence-specific, post-transcriptional, gene-silencing mechanism that is effected through double-stranded RNA (dsRNA) molecules homologous to a sequence of the target gene (Elbashir, S M et al., *Nature*

411:494-498, 2001; Fire, A et al., *Nature* 391:806-811, 1998; Tuschl, T et al., *Genes Dev* 13:3191-3197, 1999). Fragments of the dsRNA called "small interfering" RNAs (siRNAs) can rapidly induce loss of function, and only a few molecules are required in a cell to produce the effect (Fire et al., supra) through hybrid formation between a homologous siRNA and mRNA (Lin, S L et al., *Curr Cancer Drug Targets* 1:241-247, 2001). A member of the RNase III family of nucleases named dicer has been identified as being involved in processing (Bernstein, E et al., *Nature* 409:363-366, 2001). DNA vector-mediated RNAi technology has made it possible to develop therapeutic applications for use in mammalian cells (Sui, G et al., *Proc Natl Acad Sci USA* 99:5515-5520, 2002; McCaffrey, A P et al., *Nature* 418:38-39, 2002; Lee, N S et al., *Nat Biotechnol* 20:500-505, 2002). There have been several reports of delivery by retroviral vectors for stable expression (Barton, G. M et al., *Proc Natl Acad Sci USA* 99:14943-14945, 2002; Paddison, P J et al., *Cancer Cell* 2:17-23, 2002; Rubinson, D A et al., *Nat Genet* 33:401-406, 2003; Tiscornia, G et al., *Proc Natl Acad Sci USA* 100:1844-1848, 2003) or adenoviral vectors for transient expression (Xia, H et al., *Nat Biotechnol* 20:1006-1010, 2002).

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present inventors produced adenovirus vectors encoding siRNA sequences directed against both mouse and human Met and under the control of the U6 promoter. RNAi encoded by these constructs effectively silenced met RNA and protein expression in all cell types examined. The abrogation of Met strongly inhibited in vitro cell proliferation, scattering, and migration, all of which are outcomes of HGF/SF-stimulation via the Met receptor. More importantly, Met abrogation also induced apoptosis and suppressed tumor development and growth in vivo. Thus c-met siRNA vectors are useful as for targeting and treating Met expressing cancers. Since c-met is involved in the process of proliferation, invasion and metastasis in a vast range of tumor types, the present adenoviruses and other vectors carrying c-met siRNA may be directed against a particularly broad range of cancers characterized by activation of the Met signalling pathway.

The present invention is directed to a interfering RNA (RNAi) molecule having a sequence that is sufficiently complementary to the sequence of mRNA encoded by human c-met (SEQ ID NO:1) or murine c-met (SEQ ID NO:2) so that expression of the RNAi molecule in a cell that normally expresses c-met results in diminution or loss of expression of the mRNA. The RNAi molecule may be a single stranded siRNA that forms a hairpin structure or a double stranded siRNA.

It should be understood that when a nucleotide sequence is written herein with bases that include thymine (T), a characeristic of DNA, the "identical" RNA sequence contains a uracil base (U) at that position, or if a DNA coding sequence is shown, the encoded RNA sequence will have a U at a position corresponding to (complementary to) an adenine (A) of the coding sequence. Preferably, the above RNAi molecule comprises, or, in the alternative, consists essentially of, a sequences selected from the group consisting of SEQ ID NO:9; SEQ ID NO:10; SEQ ID NO:11; SEQ ID NO:12; SEQ ID NO:13; SEQ ID NO:14; and SEQ ID NO:15, or a sequence that is complementary to one of said sequences of this group.

Also provided is a DNA molecule encoding any of the above RNAi molecules.

Another embodiment provides an expression construct comprising DNA encoding the above RNAi molecule, operatively linked to a promoter that drives the expression of the RNAi in a c-met-expressing cell. The promoter is preferably one that drives the expression of the RNAi in a c-met-expressing tumor or cancer cell, such as a polIII promoter, a preferred example of which is a U6 promoter.

The invention is directed to a vector, preferably a viral vector, comprising the above expression construct. This vector can be a transient or a stable expression vector. Preferred are adenoviral vectors, in particular an Ad5 viral vector. Preferred Ad5 vectors include those encoding a human, murine or canine Met-directed siRNA: (a) si-mMet-Ad5[57]; (b) si-mMet-Ad5[60]; (c) si-mMet-Ad5[110]; (d) si-mMet-Ad5[178]; (e) si-hMet-Ad5[16]; (f) si-hMet-Ad5[62]; (g) si-hMet-Ad5[221] (h) si-dMet-Ad5[111]; (i) si-dMet-Ad5[197], and (j) si dMet-Ad5[222].

Another embodiment of the invention is a method for inhibiting c-met expression in a c-met expressing cell, comprising modifying the cell so that it expresses (a) the above RNAi molecule, (b) the above DNA molecule, or (c) the above expression construct, under conditions effective to inhibit the c-met expression. Another method comprises infecting the cell with the above viral vector under conditions that are effective for (i) expression of the RNAi molecule, and thereby (ii) inhibition for c-met expression. Preferably c-met expression is inhibited for at least 3 days after expression of the RNAi.

The cell is preferably a tumor or cancer cell, most preferably a human cell.

In the above method, the inhibiting of c-met expression reduces the ability of the cell to bind and respond to stimulation by HGF/SF.

In the above method, the RNAi molecule may be expressed in the cell in vitro or preferably, in vivo. Preferably, the cell and the expression vector reside in a subject with cancer.

Also provided is a method for inhibiting proliferation, invasion and/or metastasis of a c-met[+] tumor cell or killing the tumor cell, comprising modifying the cell so that it expresses the above RNAi molecule, DNA molecule, or expression construct, thereby inhibiting the proliferation, invasion and/ or metastasis or killing the tumor cell. The method may also comprise infecting the cell with the above viral vector in a manner effective for expression of the RNAi molecule, and inhibition for c-met expression, thereby inhibiting the proliferation, invasion and/or metastasis or killing the tumor cell, typically by apoptosis. In this method, the RNAi molecule may be expressed in vitro or, preferably, in vivo, such as in tumor cells in a subject with cancer.

The cancer that may be targeted by the above compositions and methods include several categories, as set forth in Table 1, namely, a carcinoma, a musculoskeletal sarcoma, a soft tissue sarcoma, a hematopoietic malignancy, or another cancer type (e.g., glioblastoma, astrocytomas, melanoma, mesothelioma and Wilms' tumor).

The invention includes a method of treating a c-met[+] tumor or cancer in a subject, comprising administering to the subject an amount of the above viral vector effective for inhibiting expression of c-met and thereby (i) inhibiting the growth, invasion or metastasis of cells of the tumor or cancer, or (ii) killing the tumor or cancer cells.

BRIEF DESCRIPTION OF THE DRAWINGS

FIG. 1A: M114 mouse met-transformed NIH3T3 cells were infected with four different c-met siRNA adenoviruses at multiplicity of infection ("moi") of 10, 50, and 100. After three days, cells were harvested and Met expression was determined by Western blot (20 μg protein per lane). Met expression was suppressed by si-mMet-Ad5$^{57}$ and si-mMet-Ad$^{178}$ at moi=50 and 100. No significant reduction in Met expression was observed in mock virus that has only the mU6 promoter. The strongest RNAi effect was from si-mMet-Ad5$^{178}$. FIG. 1B: DBTRG human glioblastoma cells were infected with three different constructs of c-jet siRNA adenoviruses at different moi (0, 10, 50, 100). After 3 d., cells were harvested and Met expression was determined as above. Met expression was dramatically suppressed by si-hMet-Ad5 numbers 16, 62, and 221 at moi's from 10-100. si-hMet-Ad5$^{221}$ showed the strongest RNAi effect. No reduction in Met expression was observed with mock mU6-Ad5 virus. FIG. 1C: Left panel: PC-3 human prostate cancer cells were infected with si-hMet-Ad5 viruses at moi=100. After three days, cells were harvested and the Met expression determined (30 μg protein/lane). Again si-hMet-Ad5$^{221}$ showed the strongest RNAi effect. A mixture of all three vectors (si-hMet-Ad5$^{16, 62, 221}$) at moi=33.3 each gave a similar effect. Right panel: PC-3 cells were infected with mock (mU6-Ad5) or c-met siRNA (si-hMet Ad5$^{221}$) adenoviruses at different moi (0, 10, 50, 100). Cells were harvested and Met expression determined as above (30 μg protein/lane). Met expression was suppressed by si-hMet-Ad5$^{221}$ dose dependently. FIG. 1D: MKN45 human gastric cancer cells were infected with mock (mU6-Ad5) or c-met siRNA (si-hMet-Ad5$^{221}$) adenoviruses at different moi of 0, 10, 50, and 100. Cells were harvested and Met expression determined as above (30 μg protein/lane). This cell line expresses a high level of Met. Again Met expression was dramatically suppressed by si-hMet-Ad5$^{221}$ at moi=50-100.

FIGS. 2A-2B show effects of Met siRNA adenovirus on cell morphology. FIG. 2A shows morphological changes in M114 cells after infection with c-met siRNA adenovirus. Top: M114 cells were infected with mU6-Ad5, si-mMet-Ad5$^{110}$, or si-mMet-Ad5$^{178}$ adenovirus at moi=100 and cultured for 5 d. Cells infected with si-mMet Ad5 were less refractile and more adherent (arrows). Non-infected control or mock virus-infected M114 cells remained refractile in appearance (200× magnification). Middle: M114 cells were infected with si-mMet-Ad5$^{178}$ adenovirus at different moi (0, 10, 50, and 100). After three days, cell growth was suppressed dose dependently. Again cells infected with si-mMet Ad5$^{178}$ were less refractile and more adherent (100× magnification). Bottom: To reduce the effect of cell density, si-mMet-Ad5$^{178}$-infected M114 cells were trypsinized at day 4 after infection, and each sample reseeded in a 6-well culture plate at the same cell density of (10$^5$ cells/well). Cells were observed 24 hr later. Less refractile change was dominant at moi=50-100 (100× magnification). FIG. 2B: DBTRG cells were infected with si-hMet-Ad5$^{221}$ adenovirus at moi's of 10, 50, 100. After four days, cell appearance was observed. Non-infected control cells grew well and displayed a palisade pattern. In contrast, cells infected with si-mMet-Ad5$^{221}$ were less spindle-shaped and revealed a wider cytoplasm. At the same time many cells rounded up and lost contact with the surface at moi=100 (100× magnification).

FIG. 3A shows specificity of the si-Met-Ad5 adenoviruses. DA3 mouse mammary adenocarcinoma cells were infected with mock virus and si-mMet or si-hMet-Ad5 viruses at moi=100. Met expression (day 3) was strongly suppressed only in the cells infected with si-mMet-Ad5$^{178}$; no reduction in Met protein was observed in cells infected with the most potent RNAi for human Met, si-hMet-Ad5$^{221}$. FIG. 3B: Analysis of met mRNA expression by RT-PCR. Total RNA was extracted from the DA3 cells infected with mock or si-mMet-Ad5$^{178}$ viruses at moi=100 for 3 days. Expression of met mRNA was dramatically reduced only in si-mMet-Ad5$^{178}$-infected cells. FIG. 4A DA3 cells were seeded at low cell density and cultured for 24 h and stimulated with 100 ng/ml HGF/SF for 48 h. Cell scattering was observed under a phase contrast. The DA3 scattered after treatment with HGF/SF (100× magnification). FIG. 4B: RNAi prevented HGF/SF-induced cell scattering. DA3 cells were infected with mU6-Ad5 or si-mMet-Ad5 57, 110, or 178 at moi=100 and cultured for 3 days. After reseeding, cells were cultured in low-serum medium for 24 h and treated with 100 ng/ml HGF/SF for 24 h. Cell scattering activity was suppressed in cells infected with the Ad5 viruses containing met siRNA coding sequences relative to mock infected cells (100× magnification).

FIG. 5A: M114 cells were infected with si-mMet-Ad5$^{178}$ at moi=100. Three days after infection, cells were trypsinized and reseeded (passage 1). This was repeated after three more days (passage 2). RNAi persisted even through passage 2. FIG. 5B: SK-LMS-1 cells were infected with si-hMet-Ad5$^{62}$ at moi=100 and Met expression was followed up to the second passage as described for M114 cells. No remarkable reduction in Met expression was seen 3 d after infection, but significant suppression was observed after passage 1 and through passage 2. FIG. 5C: Time course of Met reduction by c-met siRNA adenovirus. DA3 cells were infected with si-mMet-Ad5 viruses at moi=100. Cells were harvested after 24, 48, or 72 h following infection, and Met expression level was determined by Western blot. Thirty micrograms of protein was loaded in each lane. The RNAi effect was observed with all si-mMet-Ad5 viruses from 24 h to 72 h. Adenovirus si-mMet-Ad5$^{178}$ produced the strongest effect. A mixture of all three (si-mMet-Ad5$^{57, 110, 178}$) was no better. This RNAi effect lasted after cell passage, but a reduction of cell viability was observed with si-mMet-Ad5-infected cells

At day 6, dramatic increase in the apoptotic fraction was observed in DA3 and MKN45 cells.

Figure 8A:
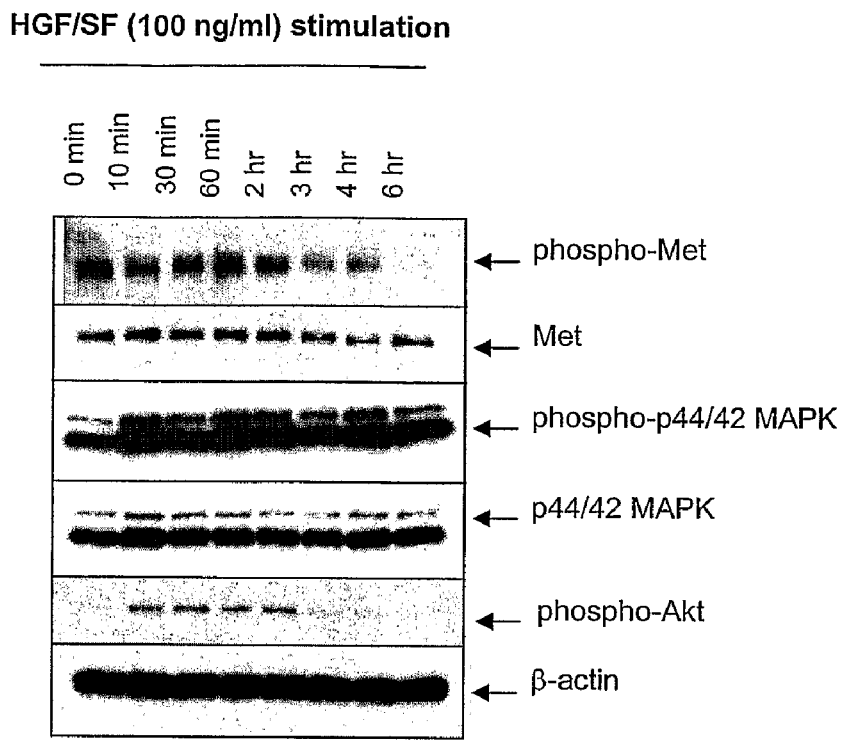
Figure 8B:
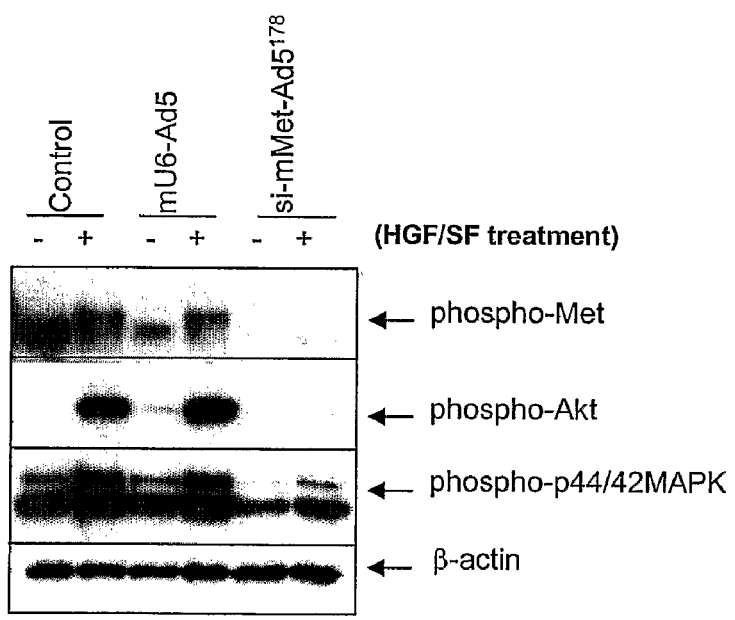

FIG. 8 shows that RNAi suppresses phosphorylation of Met and downstream signaling. FIG. 8A: DA3 cells pretreated with the serum-free medium for 24 h were stimulated with HGF/SF (100 ng/ml). Cell lysates were collected and Met, ERK1,2 (p44/42 MAPK), and Akt phosphorylation were analyzed by Western blot. In response to HGF/SF, DA3 cells showed rapid phosphorylation of Akt and p44/42 MAPK. Although some phosphorylation of Met was observed before the HGF/SF stimulation, phosphorylation increased until 2 h, then decreased gradually. FIG. 8B: DA3 cells were infected with si-mMet-Ad5[178] virus for 3 d. Cells were transferred to serum-free medium and cultured for 24 h. Cell lysates were collected 10 min after HGF/SF (100 ng/ml) treatment and protein phosphorylation was analyzed by Western blot. After HGF/SF treatment, control and mock virus-infected cells showed phosphorylation of Met, Akt, and MAPK. Phosphorylation of these molecules was marginal or inhibited in si-mMet-Ad5 virus-infected cells. There was no obvious change in the expression level of non-phosphorylated Akt in si-mMet-Ad5-infected cells.

Figure 9A:
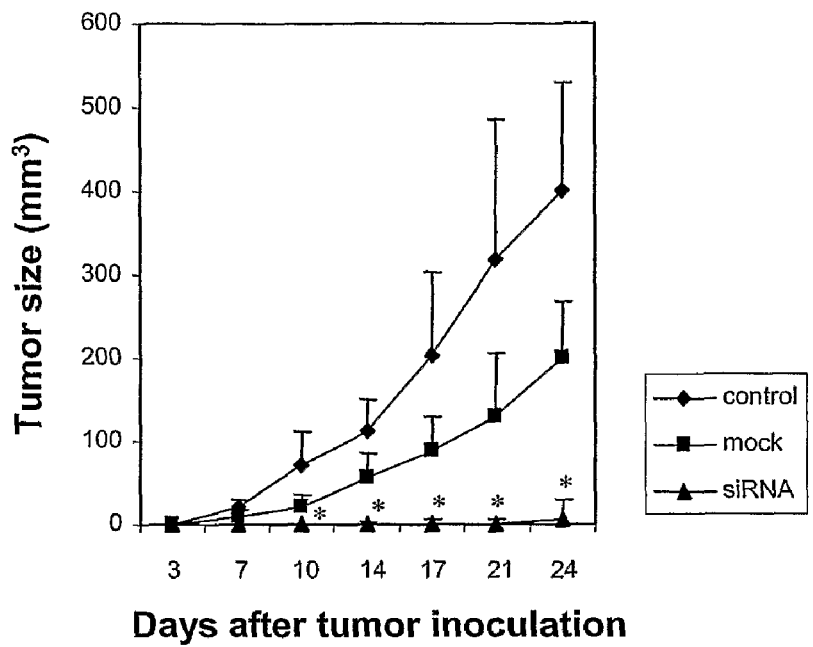
Figure 9B:
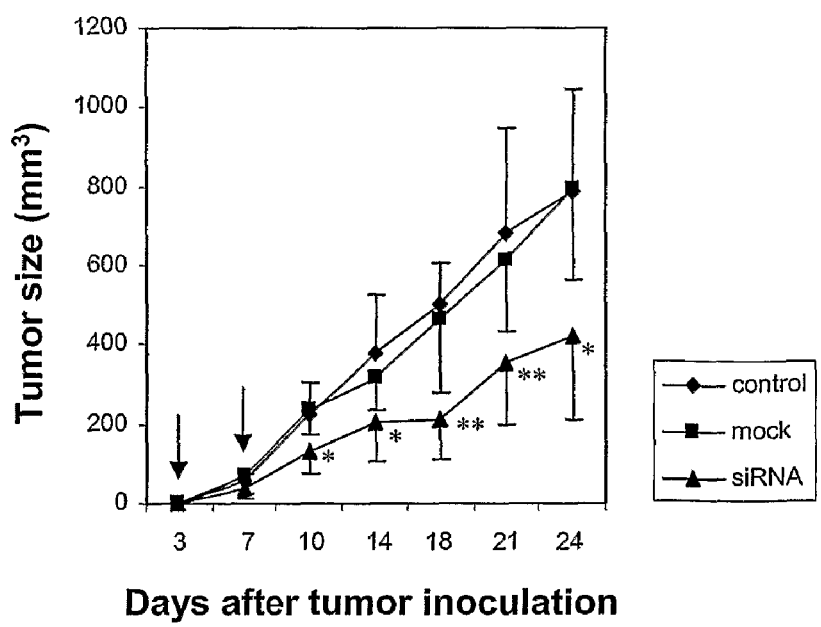

FIGS. 9A-9B show effects of c-met siRNA on in vivo tumorigenicity of DA3 cells. DA3 cells were infected with si-mMet-Ad5[178] virus in vitro at moi=100. After 3 d, cells were trypsinized and resuspended at $10^6$/ml. BALB/c mice were inoculated subcutaneously (sc) in the right flank with $10^5$ cells. Tumor size was observed and recorded twice a week. DA3 cells infected with si-mMet-Ad5[178] did not form tumors for 21 days. Each symbol and bar represents the mean±SD of 10-11 animals. *p<0.001 compared to non-infected control and p<0.01 compared to mock (mU6-Ad5) infection. FIG. 9B: DA3 cells ($10^5$) were inoculated sc into the right flanks of BALB/c mice. Three and seven days later (indicated by arrows), $4\times10^7$ pfu of si-mMet-Ad5[178] virus (in 0.1 ml PBS) was injected into the tumor lesion. Tumor size was followed and recorded for 24 days. Control: PBS only, Mock: mU6-Ad5 ($4\times10^7$ pfu). Each symbol and bar represents the mean±SD of eight to ten animals. *p<0.05 compared to PBS control and p<0.01 compared to mock (mU6-Ad5) virus treatment. **p<0.01 compared to both PBS control and mock virus treatment. There was no statistical significance between PBS control and mock virus-treated groups.

Figure 10A:
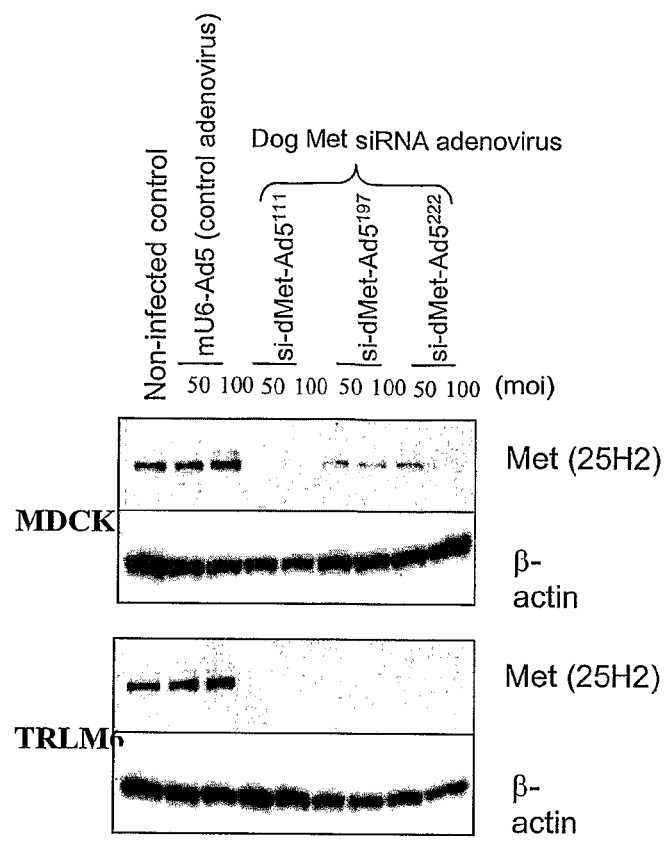
Figure 10B:
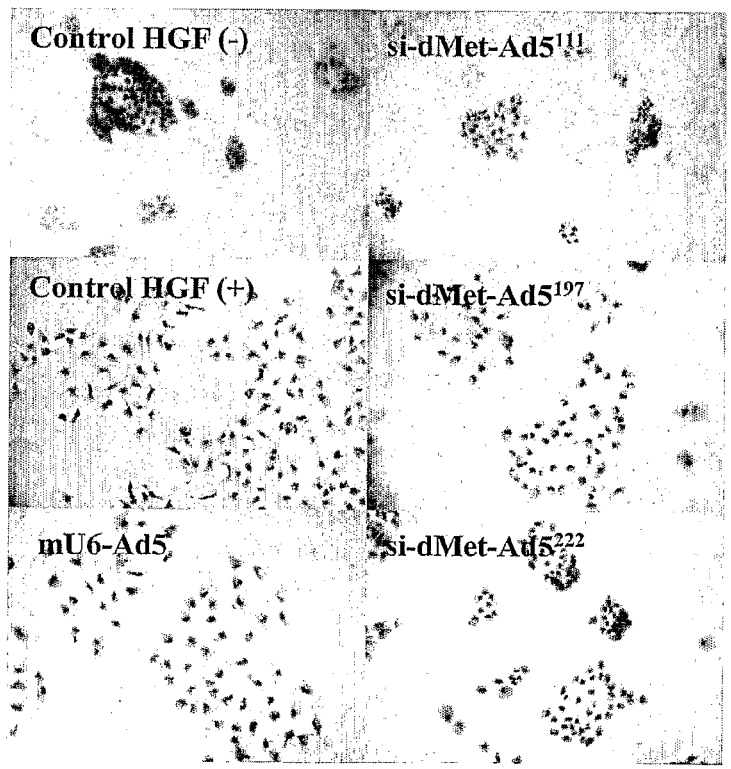

FIGS. 10A and 10B show effects of RNAi on MDCK nontransformed canine epithelial cells vs. TR6LM canine prostate carcinoma cells. FIG. 10 shows effects of dog Met siRNA adenovirus constructs on Met expression. MDCK and TRF16M cells were infected with three different constructs of Ad Met SiRNA at different moi's (50 and 100). After 3 days, cells were harvested and met expression level was observed by Western blot. Thirty μg of protein was loaded in each lane. FIG. 10B is a series of micrographs showing effects of dMet-Ad5 adenoviruses on the scattering of MDCK cells. MDCK cells were infected with mnU6-AD5 or si-dMet-Ad5[111, 197 or 222] at moi=5 and cultured for 3 days. After reseeding, cells were cultured for 24 hrs and treated with 25 mg/ml HGF/SF for 24 hrs. Cell scattering activity was suppressed in a Met-dependent manner (100× magnification).

Figure 11A:
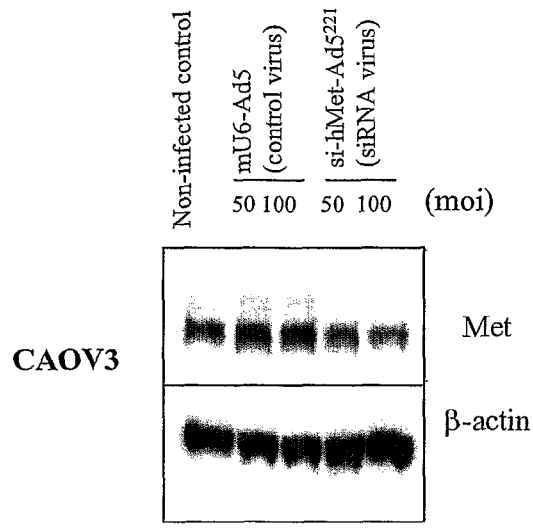
Figure 11C:
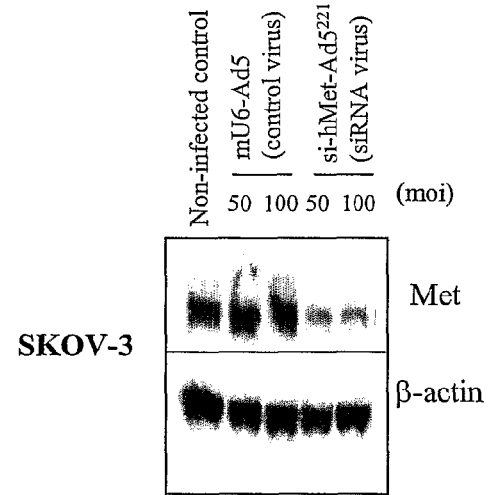
Figure 11B:
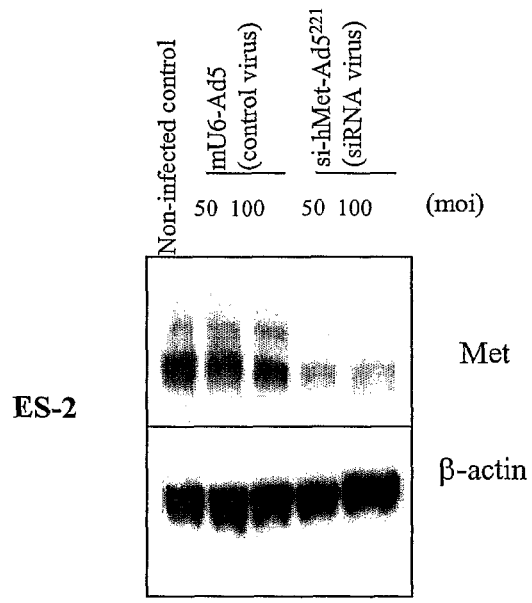
Figure 11D:
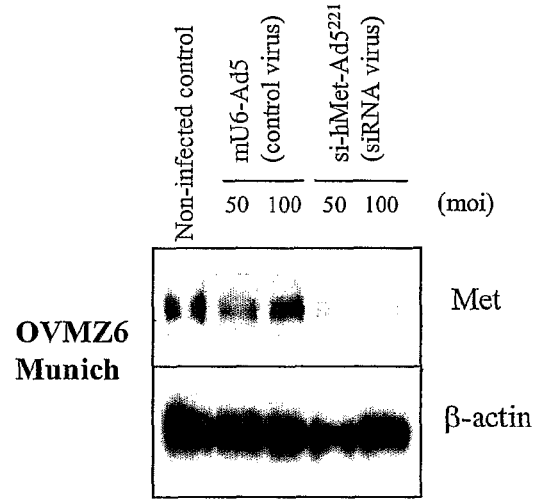

FIGS. 11A-11D show effects of c-met siRNA adenovirus infection on Met expression in human ovarian cancer. The following three human ovarian carcinoma cell lines were used: CAOV3, ES2, SKOV-3 and OVMZ6 (Munich). Western blots are shown, as described for FIG. 1A-D and in Example 1. Western blot was done on day 4 after infection with the human Met-directed constructm, si-hMet-Ad5[221] (30 mg protein/lane) (FIGS. 11A, B and D). SKOV-3 cells (FIG. 11C) were infected with the adenovirus while in suspension, and cells were then plated in culture dish.

DESCRIPTION OF THE PREFERRED EMBODIMENTS

The present inventors designed vectors that express siRNA sequences that hybridize to, and block activation of c-Met, a protein tyrosine kinase receptor for HGF/SF. The present invention is directed to the siRNA molecules (sequences), vectors, preferably adenovirus vectors, with a promoter, exemplified by the U6 promoter, that drives transcription of siRNA sequences that are "specific" for sequences of c-met nucleic acid. siRNA "hairpin" sequences are preferred because of their stability and binding to the target mRNA.

Since c-met is involved in the process of proliferation, invasion and metastasis in a vast range of tumor types, the present adenoviruses carrying c-met siRNA may be directed against a particularly broad range of cancers characterized by activation of the Met signalling pathway. A nonlimiting list of such cancers appears in Table 1.

TABLE 1

List of Met-Expressing Cancers*

| Category | Cancer Type | HGF/SF expression | Poor Prognosis | Mutation of Met |
|---|---|---|---|---|
| Carcinomas | Bladder | + | + | − |
| | Breast | + | + | − |
| | Cervical | + | + | − |
| | Colorectal | + | − | − |
| | Esophageal | − | − | − |
| | Gastric | + | + | + |
| | Head and Neck | + | + | + |
| | Kidney | + | − | + |
| | Liver | + | + | + |
| | Lung | + | + | + |
| | Nasopharyngeal | + | + | − |
| | Ovarian | − | − | + |
| | Pancreas/Gall Bladder | + | − | − |
| | Prostate | + | − | − |
| | Thyroid | + | + | − |
| Musculoskeletal sarcomas | Osteosarcoma | + | − | − |
| | Synovial Sarcoma | + | + | − |
| | Rhabdomyosarcoma | − | − | − |
| Soft tissue sarcomas | MFH/Fibrosarcoma | + | − | − |
| | Leiomyosarcoma | + | − | − |
| | Kaposi's Sarcoma | + | − | − |
| Hematopoietic Malignancies | Multiple Myeloma | + | + | − |
| | Lymphomas | + | − | − |
| | Adult T Cell Leukemia | − | − | − |
| | Glioblastomas/ Astrocytomas | + | + | + |
| Other Neoplasms | Melanoma | + | − | − |
| | Mesothelioma | + | − | − |
| | Wilms' Tumor | + | − | − |

*many of these express HGF/SF, indicating autocrine stimulation of the Met pathway.
For each cancer type, headings correspond to studies showing: HGF/SF expression in tumor biopsies; Met expression in tumor biopsies; expression of HGF/SF or Met correlating with poor prognosis; sporadic or germline-activating mutations in Met; tumor cells in vitro expressing Met or HGF/SF, some with correlation to in vitro neoplastic-like activities; and animal models supporting the role of Met and HGF/SF in cancer, including humantumor xenografts in immune-compromised mice, mice with HGF/SF or Met transgenes, or other animal models displaying dependence on HGF/SF or Met in cancer development. MFH = malignant fibrous histiocytoma;
+ indicates "Yes" for HGF/SF expression, poor prognosis and presence of Met mutation;
− indicates no report of HGF/SF expression, poor prognosis or presence of Met mutation Human and Murine cMet The human met gene nucleotide sequence (hmet) is shown below (SEQ ID NO:1) and has the Genbank accession number NM_000245. The coding sequence begins at nt 189 and continues up to nt 4415 (the last 5 nt's leading up to this point are boldfaced below. The signal peptide is encoded by nt's 189-260 and the met protooncogene product is encoded by nt's 261-4412. The HGF receptor α chain is encoded by nt's 261-1097 (underscored, all caps). The HGF receptor β chain is encoded by nt's 1110-4358 (underscored low case).

```
   1 cgccctcgcc gcccgcggcg ccccgagcgc tttgtgagca
     gatgcggagc cgagtggagg 61 gcgcgagcca gatgcgggc  gacagctgac ttgctgagag
     gaggcgggga ggcgcggagc 121 gcgcgtgtgg tccttgcgcc gctgacttct ccactggttc
     ctgggcaccg aaagataaac 181 ctctcataat gaaggccccc gctgtgcttg cacctggcat
     cctcgtgctc ctgtttacct 241 tggtgcagag gagcaatggg GAGTGTAAAG AGGCACTAGC
     AAAGTCCGAG ATGAATGTGA

301 ATATGAAGTA TCAGCTTCCC AACTTCACCG CGGAAACACC
     CATCCAGAAT GTCATTCTAC

361 ATGAGCATCA CATTTTCCTT GGTGCCACTA ACTACATTTA
     TGTTTTAAAT GAGGAAGACC

421 TTCAGAAGGT TGCTGAGTAC AAGACTGGGC CTGTGCTGGA
     ACACCCAGAT TGTTTCCCAT

481 GTCAGGACTG CAGCAGCAAA GCCAATTTAT CAGGAGGTGT
     TTGGAAAGAT AACATCAACA

541 TGGCTCTAGT TGTCGACACC TACTATGATG ATCAACTCAT
     TAGCTGTGGC AGCGTCAACA

601 GAGGGACCTG CCAGCGACAT GTCTTTCCCC ACAATCATAC
     TGCTGACATA CAGTCGGAGG

661 TTCACTGCAT ATTCTCCCCA CAGATAGAAG AGCCCAGCCA
     GTGTCCTGAC TGTGTGGTGA

721 GCGCCCTGGG AGCCAAAGTC CTTTCATCTG TAAAGGACCG
     GTTCATCAAC TTCTTTGTAG

781 GCAATACCAT AAATTCTTCT TATTTCCCAG ATCATCCATT
     GCATTCGATA TCAGTGAGAA

841 GGCTAAAGGA AACGAAAGAT GGTTTTATGT TTTTGACGGA
     CCAGTCCTAC ATTGATGTTT

901 TACCTGAGTT CAGAGATTCT TACCCCATTA AGTATGTCCA
     TGCCTTTGAA AGCAACAATT

961 TTATTTACTT CTTGACGGTC CAAAGGGAAA CTCTAGATGC
     TCAGACTTTT CACACAAGAA

1021 TAATCAGGTT CTGTTCCATA AACTCTGGAT TGCATTCCTA
     CATGGAAATG CCTCTGCAGT

1081 GTATTCTCAC AGAAAAGaga aaaaagagat ccacaaagaa
     ggaagtgttt aatatacttc 1141 aggctgcgta tgtcagcaag cctggggccc agcttgctag
     acaaatagga gccagcctga 1201 atgatgacat tcttttcggg gtgttcgcac aaagcaagcc
     agattctgcc gaaccaatgg 1261 atcgatctgc catgtgtgca ttccctatca aatatgtcaa
     cgacttcttc aacaagatcg 1321 tcaacaaaaa caatgtgaga tgtctccagc attttacgg
     acccaatcat gagcactgct 1381 ttaataggca acttctgaga aattcatcag gctgtgaagc
     gcgccgtgat gaatatcgaa 1441 cagagtttac cacagctttg cagcgcgttg acttattcat
     gggtcaattc agcgaagtcc 1501 tcttaacatc tatatccacc ttcattaaag gagacctcac
     catagctaat cttgggacat 1561 cagagggtcg cttcatgcag gttgtggttt ctcgatcagg
     accatcaacc cctcatgtga 1621 attttctcct ggactccat ccagtgtctc cagaagtgat
     tgtggagcat acattaaacc 1681 aaaatggcta cactgggtt atcactggga gaagatcac
     gaagatccca ttgaatggct 1741 tgggctgcag acatttccag tcctgcagtc aatgcctctc
     tgccccaccc tttgttcagt 1801 gtggctggtg ccacgacaaa tgtgtgcgat cggaggaatg
     cctgagcggg acatggactc 1861 aacagatctg tctgcctgca atctacaagg ttttcccaaa
     tagtgcaccc cttgaaggag 1921 ggacaaggct gaccatatgt ggctgggact ttggatttcg
     gaggaataat aaatttgatt 1981 taaagaaaac tagagttctc cttggaaatg agagctgcac
     cttgactta agtgagagca 2041 cgatgaatac attgaaatgc acagttggtc ctgccatgaa
     taagcatttc aatatgtcca 2101 taattatttc aaatggccac gggacaacac aatacagtac
     attctcctat gtggatcctg 2161 taataacaag tatttcgccg aaatacggtc ctatggctgg
     tggcactttta cttactttaa 2221 ctgaaattta cctaaacagt gggaattcta gacacatttc
     aattggtgga aaaacatgta 2281 cttaaaaag tgtgtcaaac agtattcttg aatgttatac
     cccagcccaa accatttcaa 2341 ctgagtttgc tgttaaattg aaaattgact tagccaaccg
     agagacaagc atcttcagtt 2401 accgtgaaga tcccattgtc tatgaaattc atccaaccaa
     atcttttatt agtacttggt 2461 ggaaagaacc tctcaacatt gtcagttttc tattttgctt
     tgccagtggt gggagcacaa 2521 taacaggtgt tgggaaaaac ctgaattcag ttagtgtccc
     gagaatggtc ataaatgtgc 2581 atgaagcagg aaggaacttt acagtggcat gtcaacatcg
     ctctaattca gagataatct 2641 gttgtaccac tccttccctg caacagctga atctgcaact
     cccctgaaa accaaagcct 2701 ttttcatgtt agatgggatc ctttccaaat actttgatct
     catttatgta cataatcctg 2761 tgtttaagcc ttttgaaaag ccagtgatga tctcaatggg
     caatgaaaat gtactggaaa 2821 ttaagggaaa tgatattgac cctgaagcag ttaaaggtga
     agtgttaaaa gttggaaata 2881 agagctgtga gaatatacac ttacattctg aagccgtttt
     atgcacggtc cccaatgacc 2941 tgctgaaatt gaacagcgag ctaaatatag agtggaagca
     agcaatttct tcaaccgtcc 3001 ttggaaaagt aatagttcaa ccagatcaga atttcacagg
     attgattgct ggtgttgtct
```

```
-continued 3061 caatatcaac agcactgtta ttactacttg ggttttttcct
     gtggctgaaa aagagaaagc 3121 aaattaaaga tctgggcagt gaattagttc gctacgatgc
     aagagtacac actcctcatt 3181 tggataggct tgtaagtgcc cgaagtgtaa gcccaactac
     agaaatggtt tcaaatgaat 3241 ctgtagacta ccgagctact tttccagaag atcagtttcc
     taattcatct cagaacggtt 3301 catgccgaca agtgcagtat cctctgacag acatgtcccc
     catcctaact agtggggact 3361 ctgatatatc cagtccatta ctgcaaaata ctgtccacat
     tgacctcagt gctctaaatc 3421 cagagctggt ccaggcagtg cagcatgtag tgattgggcc
     cagtagcctg attgtgcatt 3481 tcaatgaagt cataggaaga gggcattttg gttgtgtata
     tcatgggact ttgttggaca 3541 atgatggcaa gaaaattcac tgtgctgtga aatccttgaa
     cagaatcact gacataggag 3601 aagtttccca atttctgacc gagggaatca tcatgaaaga
     ttttagtcat cccaatgtcc 3661 tctcgctcct gggaatctgc ctgcgaagtg aagggtctcc
     gctggtggtc ctaccataca 3721 tgaaacatgg agatcttcga aatttcattc gaaatgagac
     tcataatcca actgtaaaag 3781 atcttattgg cttggtct caagtagcca aagcgatgaa
     atatcttgca agcaaaaagt 3841 ttgtccacag agacttggct gcaagaaact gtatgctgga
     tgaaaaattc acagtcaagg 3901 ttgctgattt tggtcttgcc agagacatgt atgataaaga
     atactatagt gtacacaaca 3961 aaacaggtgc aaagctgcca gtgaagtgga tggctttgga
     aagtctgcaa actcaaaagt 4021 ttaccaccaa gtcagatgtg tggtcctttg gcgtcgtcct
     ctgggagctg atgacaagag 4081 gagcccacc ttatcctgac gtaaacacct ttgatataac
     tgtttacttg ttgcaaggga 4141 gaagactcct acaacccgaa tactgcccag acccccttata
     tgaagtaatg ctaaaatgct 4201 ggcacccta agccgaaatg cgcccatcct tttctgaact
     ggtgtcccgg atatcagcga 4261 tcttctctac tttcattggg gagcactatg tccatgtgaa
     cgctacttat gtgaacgtaa 4321 aatgtgtcgc tccgtatcct tctctgttgt catcagaaga
     taacgctgat gatgaggtgg 4381 acacacgacc agcctccttc tgggagacat catagtgcta
     gtactatgtc aaagcaacag 4441 tccacacttt gtccaatggt ttttttcactg cctgacctttt
     aaaaggccat cgatattctt 4501 tgctccttgc cataggactt gtattgttat ttaaattact
     ggattctaag gaatttctta 4561 tctgacagag catcagaacc agaggcttgg tcccacaggc
     cagggaccaa tgcgctgcag
```

The amino acid sequence of the human Met protein (1408 residues) is shown below (SEQ ID NO:2).

```
   MKAPAVLAPG ILVLLFTLVQ RSNGECKEAL AKSEMNVNMK
   YQLPNFTAET PIQNVILHEH HIFLGATNYI YVLNEEDLQK
   VAEYKTGPVL EHPDCFPCQD CSSKANLSGG VWKDNINMAL
   VVDTYYDDQL ISCGSVNRGT CQRHVFPHNH TADIQSEVHC
   IFSPQIEEPS QCPDCVVSAL GAKVLSSVKD RFINFFVGNT
   INSSYFPDHP LHSISVRRLK ETKDGFMFLT DQSYIDVLPE
   FRDSYPIKYV HAFESNNFIY FLTVQRETLD AQTFHTRIIR
   FCSINSGLHS YMEMPLECIL TEKRKKRSTK KEVFNILQAA
   YVSKPGAQLA RQIGASLNDD ILFGVFAQSK PDSAEPMDRS
   AMCAFPIKYV NDFFNKIVNK NNVRCLQHFY GPNHEHCFNR
   TLLRNSSGCE ARRDEYRTEF TTALQRVDLF MGQFSEVLLT
   SISTFIKGDL TIANLGTSEG RFMQVVVSRS GPSTPHVNFL
   LDSHPVSPEV IVEHTLNQNG YTLVITGKKI TKIPLNGLGC
   RHFQSCSQCL SAPPFVQCGW CHKDCVRSEE CLSGTWTQQI
   CLPAIYKVFP NSAPLEGGTR LTICGWDFGF RRNNKFDLKK
   TRVLLGNESC TLTLSESTMN TLKCTVGPAM NKHFNMSIII
   SNGHGTTQYS TFSYVDPVIT SISPKYGPMA GGTLLTLTGN
   YLNSGNSRHI SIGGKTCTLK SVSNSILECY TPAQTISTEF
   AVKLKIDLAN RETSIFSYRE DPIVYEIHPT KSFISTWWKE
   PLNIVSFLFC FASGGSTITG VGKNLNSVSV PRMVINVHEA
   GRNFTVACQH RSNSEIICCT TPSLQQLNLQ LPLKTKAFFM
   LDGILSKYFD LIYVHNPVFK PFEKPVMISM GNENVLEIKG
   NDIDPEAVKG EVLKVGNKSC ENIHLHSEAV LCTVPNDLLK
   LNSELNIEWK QAISSTVLGK VIVQPDQNFT GLIAGVVSIS
   TALLLLLGFF LWLKKRKQIK DLGSELVRYD ARVHTPHLDR
   LVSARSVSPT TEMVSNESVD YRATFPEDQF PNSSQNGSCR
   QVQYPLTDMS PILTSGDSDI SSPLLQNTVH IDLSALNPEL
   VQAVQHVVIG PSSLIVHFNE VIGRGHFGCV YHGTLLDNDG
   KKIHCAVKSL NIRTDIGEVS QFLTEGIIMK DFSHPNVLSL
   LGICLRSEGS PLVVLPYMKH GDLRNFIRNE THNPTVKDLI
   GFGLQVAKAM KYLASKKFVH RDLAARNCML DEKFTVKVAD
   FGLARDMYDK EYYSVHNKTG AKLPVKWMAL ESLQTQKFTT
   KSDVWSFGVV LWELMTRGAP PYPDVNTFDI TVYLLQGRRL
   LQPEYCPDPL YEVMLKCWHP KAEMRPSFSE LVSRISAIFS
   TFIGEHYVHV NATYVNVKCV APYPSLLSSE DNADDEVDTR
   PASFWETS 1408
```

The murine c-met gene nt sequence is shown below (SEQ ID NO:3). This is the coding sequence (total of 4841 nt's)

```
   1 atgaaggctc ccaccgtgct ggcacctggc attctggtgc
     tgctgttgtc cttggtgcag 61 aggagccatg gggagtgcaa ggaggcccta gtgaagtctg
     agatgaacgt gaacatgaag 121 tatcagctcc ccaacttcac ggcagaaacc cccatccaga
     atgtcgtcct acacggccat 181 catatttatc tcggagccac aaactacatt tatgttttaa
     atgacaaaga ccttcagaag 241 gtatccgaat tcaagaccgg gcccgtgttg gaacacccag
     attgtttacc ttgtcgggac 301 tgcagcagca aagccaattc atcaggaggg gtttggaaag
     acaacatcaa catggctctg 361 cttgttgaca catactatga tgatcaactc attagctgtg
     gcagtgtcaa cagagggact 421 tgccagcggc atgtccttcc tcctgacaat tctgctgaca
     tccagtctga ggtccactgc 481 atgttctccc cagaagagga gtcagggcag tgtcctgact
     gtgtagtgag tgccctcgga 541 gccaaagtcc tcctgtcgga aaaggaccgg ttcatcaatt
     tctttgtggg gaatacgatc 601 aattcctcct atcctcctgg ttattcactg cattcgatat
     cggtgagacg gctgaaggaa 661 acccaagatg gttttaagtt tttgacagac cagtcctata
     ttgatgtctt accagaattc
```

-continued

```
 721 caagattcct accccataaa gtacatacat gccttcgaaa
     gcaaccattt tatttacttt 781 ctgactgtcc aaaaggaaac tctagatgct cagacttttc
     atacaagaat aatcaggttc 841 tgttccgtag actctgggtt gcactcctac atggaaatgc
     ccctggaatg catcctgaca 901 gaaaaagaa ggaagagatc cacaagggaa gaagtgttta
     atatcctcca agccgcgtat 961 gtcagtaaac caggggccaa tcttgctaag caaataggag
     ctagcccttc tgatgacatt 1021 ctcttcgggg tgtttgcaca aagcaagcca gattctgctg
     aacctgtgaa tcgatcagca 1081 gtctgtgcat tccccatcaa atatgtcaat gacttcttca
     acaagattgt caacaaaaac 1141 aacgtgagat gtctccagca ttttttacgga cccaaccatg
     agcactgttt caataggacc 1201 ctgctgagaa actcttccgg ctgtgaagcg cgcagtgacg
     agtatcggac agagttttacc 1261 acggctttgc agcgcgtcga cttattcatg ggccggctta
     accaagtgct cctgacatcc 1321 atctccacct tcatcaaagg tgacctcacc attgctaatc
     tagggacgtc agaaggtcgc 1381 ttcatgcagg tggtgctctc tcgaacagca cacctcactc
     ctcatgtgaa cttcctcctg 1441 gactcccatc ctgtatctcc agaagttatt gttgagcatc
     catcaaatca aaatggctat 1501 acattggttg tcacaggaaa gaagatcacc aagattccat
     tgaatggcct gggctgtgga 1561 catttccaat cctgcagtca gtgcctctct gccccttact
     ttatacagtg tggctggtgc 1621 cacaatcaat gtgtgcgttt tgatgaatgc cccagcggta
     catggactca agagatctgt 1681 ctgccggcgg tttataaggt gttccccacc agcgcgcccc
     ttgaaggagg aacagtgttg 1741 accatatgtg gctgggactt tggattcagg aagaataata
     aatttgattt aaggaaaacc 1801 aaagttctgc ttggcaacga gagctgtacc ttgaccttaa
     gcgagagcac gacaaatacg 1861 ttgaaatgca cagttggtcc cgcgatgagt gagcacttca
     atgtgtctgt aattatctca 1921 aacagtcgag agacgacgca atacagtgca ttctcctatg
     tagatcctgt aataacaagc 1981 atttctccga ggtacggccc tcaggctgga ggcaccttac
     tcactcttac tgggaaatac 2041 ctcaacagtg gcaattctag acacatttca attggaggga
     aaacatgtac tttaaaaagt 2101 gtatcagata gtattcttga atgatacacc ccagcccaaa
     ctacctctga tgagtttcct 2161 gtgaaattga agattgactt ggctaaccga gagaccagca
     gcttcagtta ccgggaagac 2221 cccgttgtct atgaaatcca cccgaccaaa tctttttatta
     gtggtggaag cacaataacg
```

```
2281 ggtattggga agaccctgaa ctcggttagc ctcccaaagc
     tggtaataga tgtgcatgaa 2341 gtgggtgtga actacacagt ggcatgtcag catcgctcaa
     attcagagat catctgctgc 2401 actactcctt cactgaaaca gctgggcctg caactcccc
     tgaagaccaa agccttcttc 2461 ctgttagacg ggattctttc caaacacttt gatctcactt
     atgtgcataa tcctgtgttt 2521 gagcctttg aaaagccagt aatgatctca ataggcaatg
     aaaatgtagt ggaaattaag 2581 ggaaacaata ttgaccctga agcagttaaa ggtgaagtgt
     taaaagttgg aaatcagagc 2641 tgcgagagtc tccactggca ctctggagct gtgttgtgta
     cagtccccag tgacctgctc 2701 aaactgaaca gcgagctaaa tatagagtgg aagcaagcag
     tctcttcaac tgttcttgga 2761 aaagtgatcg ttcaaccgga tcagaatttt gcaggattga
     tcattggtgc ggtctcaata 2821 tcagtagtag ttttgttatt atccgggctc ttcctgtgga
     tgagaaagag aaagcataaa 2881 gatctgggca gtgaattagt tcgctatgac gcaagagtac
     acactcctca tttggatagg 2941 cttgtaagtg cccgaagtgt aagtccaact acagagatgg
     tttcaaatga gtctgtagac 3001 tacagagcta cttttccaga agaccagttt cccaactcct
     ctcagaatgg agcatgcaga 3061 caagtgcaat accctctgac agacctgtcc cctatcctga
     caagtggaga ctctgatata 3121 tccagcccat tactacaaaa tactgttcac attgacctca
     gtgctctaaa tccagagctg 3181 gtccaagcag ttcagcacgt agtgattgga cccagcagcc
     tgattgtgca tttcaatgaa 3241 gtcataggaa gagggcattt tggctgtgtc tatcatggga
     ctttgctgga caatgacgga 3301 aagaaaattc actgtgctgt gaaatcctta aatagaatca
     cagatataga agaggtctcc 3361 cagtttctga ctgagggaat catcatgaaa gacttcagcc
     atcccaatgt tctctcactc 3421 ttgggaatct gcctgaggag tgaagggtct cctctggtgg
     tcctgcccta tatgaagcat 3481 ggagatctgc gaaatttcat tcgaaacgag actcataatc
     caactgtgaa agatcttata 3541 ggatttggcc ttcaagtagc caaaggcatg aaatatcttg
     ccagcaaaaa gttttgtccac 3601 agagacttag ctgcaagaaa ctgcatgttg gatgaaaaat
     tcactgtcaa ggttgctgat 3661 ttcggtcttg ccagagacat gtacgataaa gagtactata
     gtgtccacaa caagacgggt 3721 gccaagctac cagtaaagtg gatggcttta gagagtctgc
     aaacgcagaa gttcaccacc 3781 aagtcagatg tgtggtcctt tggtgtgctc ctctgggagc
     tcatgacgag aggagcccct
```

-continued

```
3841 ccttatcccg acgtgaacac atttgatatc actatctacc
     tgttgcaagg cagaagactc 3901 ttgcaaccag aatactgtcc agacgccttg tacgaagtga
     tgctaaaatg ctggcacccc 3961 aaagcggaaa tgcgcccgtc cttttccgaa ctggtctcca
     ggatatcctc aatcttctcc 4021 acgttcattg gggaacacta cgtccacgtg aacgctactt
     atgtgaatgt aaaatgtgtt 4081 gctccatatc cttctctgtt gccatcccaa gacaacattg
     atggcgaggg gaacacatga
```

The 1379 amino acid sequence of the murine c-Met polypeptide encoded by the foregoing murine nucleotide sequence is shown below (SEQ ID NO:4).

```
MKAPTVLAPG ILVLLLSLVQ RSHGECKEAL VKSEMNVNMK
YQLPNFTAET PIQNVVLHGH KIYLGATNYI YVLNDKDLQK
VSEFKTGPVL EHPDCLPCRD CSSKANSSGG VWKDNINMAL
LVDTYYDDQL ISCGSVNRGT CQRNVLPPDN SADIQSEVHC
MFSPEEESGQ CPDCVVSALG AKVLLSEKDR FINFFVGNTI
NSSYPPGYSL HSISVRRLKE TQDGRKFLTD QSYIDVLPEF
QDSYPIKYIH AFESNHFIYF LTVQKETLDA QTFHTRIIRF
CSVDSGLHSY MEMPLECILT EKRRKRSTRE EVFNILQAAY
VSKPGANLAK QIGASPSDDI LFGVFAQSKP DSAEPVNRSA
VCAFPIKYVN DFFNKIVNKN NVRCLQHFYG PNHEHCFNRT
LLRNSSGCEA RSDEYRTEFT TALQRVDLFM GRLNQVLLTS
ISTFIKGDLT IANLGTSEGR FMQVVLSRTA HLTPHVNFLL
DSHPVSPEVI VEHPSNQNGY TLVVTGKKIT KIPLNGLGCG
HFQSCSQCLS APYFIQCGWC HNQCVRFDEC PSGTWTQEIC
LPAVYKVFPT SAPLEGGTVL ITCGWDFGFR KNNKFDLRKT
KVLLGNESCT LTLSESTTNT LKCTVGPAMS EHFNVSVIIS
NSRETTQYSA FSYVDPVITS ISPRYGPQAG GTLLTLTGKY
LNSGNSRHIS IGGKTCTLKS VSDSILECYT PAQTTSDEFP
VKLKIDLANR ETSSFSYRED PVVYEIHPTK SFISGGSTIT
GIGKTLNSVS LPKLVIDVHE VGVNYTVACQ HRSNSEIICC
TTPSLKQLGL QLPLKTKAFF LLDGILSKHF DLTYVHNPVF
EPFEKPVMIS IGNENVVEIK GNNIDPEAVK GEVLKVGNQS
CESLHWHSGA VLCTVPSDLL KLNSELNIEW KQAVSSTVLG
KVIVQPDQNF AGLIIGAVSI SVVVLLLSGL PFWMRKRKHK
DLGSELVRYD ARVHTPHLDR LVSARSVSPT TEMVSNESVD
YRATPFEDQF PNSSQNGACR QVQYPLTDLS PILTSGDSDI
SSPLLQNTVH IDLSALNPEL VQAVQHVVIG PSSLIVHFNE
VIGRGHFGCV YHGTLLDNDG KKIHCAVKSL NRITDIEEVS
QFLTEGIIMK DFSHPNVLSL LGICLRSEGS PLVVLPYMKH
GDLRNFIRNE THNPTVKDLI GFGLQVAKGM KYLASKKFVH
RDLAARNCML DEKFTVKVAD FGLARDMYDK EYYSVHNKTG
AKLPVKWMAL ESLQTQKFTT KSDVWSFGVL LWELMTRGAP
PYPDVNTFDI TIYLLQGRRL LQPEYCPDAL YEVMLKCWHP
KAEMRPSFSE LVSRISSIFS TFIGEHYVHV NATYVNVKCV
APYPSLLPSQ DNIDGEGNT 1379
``` siRNAs siRNAs suppress gene expression through a highly regulated enzyme-mediated process called RNA interference (RNAi) (Sharp, P. A., *Genes Dev.* 15:485-490 (2001); Bernstein, E et al., *Nature* 409:363-366 (2001); Nykanen, A et al., *Cell* 107:309-321 (2001); Elbashir, S. M. et al., *Genes Dev.* 15:188-200 (2001)). RNAi involves multiple RNA-protein interactions characterized by four major steps: assembly of siRNA with the RNA-induced silencing complex (RISC), activation of the RISC, target recognition and target cleavage. These interactions may bias strand selection during siRNA-RISC assembly and activation, and contribute to the overall efficiency of RNAi (Khvorova, A et al., *Cell* 115:209-216 (2003); Schwarz, D S et al. 115:199-208 (2003)))

Two publications that describe preferred approaches and algorithms for selecting siRNA sequences are: Far, R K et al., Nuc Acids Res, 2003, 314417-4424 and Reynolds, A et al., Nature Biotech. 2004, 22:326-330. Far et al. suggests options for assessing target accessibility for siRNA and supports the design of active siRNA constructs. This approach can be automated, adapted to high throughput and is open to include additional parameters relevant to the biological activity of siRNA. To identify siRNA-specific features likely to Contribute to efficient processing at each of the steps pf RNAi noted above, Reynolds et al., supra performed a systematic analysis of 180 siRNAs targeting the mRNA of two genes. Eight characteristics associated with siRNA functionality were identified: low G/C content, a bias towards low internal stability at the sense strand 3'-terminus, lack of inverted repeats, and sense strand base preferences (positions 3, 10, 13 and 19). Application of an algorithm incorporating all eight criteria significantly improves potent siRNA selection. This highlights the utility of rational design for selecting potent siRNAs that facilitate functional gene knockdown.

Candidate siRNA sequences against mouse and human c-met are selected using a process that involves running a BLAST search against the sequence of c-met, and selecting &sequences that "survive" to ensure that these sequences will not be cross matched with any other genes.

siRNA sequences selected according to such a process and algorithm may be cloned into an expression plasmid and tested for their activity in abrogating Met function in Met-expressing cells of the appropriate animal species. Those sequences that show RNAi activity are preferably recloned into a replication-defective human adenovirus serotype 5 (Ad5).

One reason for selection of this viral vector the high titer obtainable (in the range of $10^{10}$) and therefore the high multiplicities-of infection that can be attained. For example, infection with 100 infectious units/cell ensures all cells are infected. Another advantage of this virus is the high susceptibility and infectivity and the host range (with respect to cell types). Even if expression is transient, cells can go through multiple replication cycles before Met activity recovers (see Examples).

Moreover, some tumors undergo apoptosis in response to expression of the present siRNAs, so that even transient expression is adequate to kill the cells.

Preferred constructs described in the Examples are the following:
(a) si-mMet-Ad5[178] which exerted the most dramatic effect on DA3 mouse mammary adenocarcinoma cells and M114 fibroblast cells,
(b) si-hMet-Ad5[221] which had the strongest effects on human glioblastoma cells (using the line DBTRG as an example), human prostate cancer cells (using PC-3 as an example) and human gastric cancer cells (using MKN45 as an example).

Preferred viral vectors are those with prolonged suppressive effect again st Met, lasting beyond passage of the cells in culture.

In a most preferred embodiment, the inhibitory molecule is a double stranded nucleic acid (preferably an RNA), used in a method of RNA interference. RNA interference is the sequence-specific degradation of homologues in an mRNA of a targeting sequence in an siNA. As used herein, the term siNA (small, or short, interfering nucleic acid) is meant to be equivalent to other terms used to describe nucleic acid molecules that are capable of mediating sequence specific RNAi (RNA interference), for example short (or small) interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), translational silencing, and others. Long double stranded interfering RNAs, such a miRNAs, appear to tolerate mismatches more readily than do short double stranded RNAs. In addition, as used herein, the term RNAi is meant to be equivalent to other terms used to describe sequence specific RNA interference, such as post transcriptional gene silencing, or an epigenetic phenomenon. For example, siNA molecules of the invention can be used to epigenetically silence genes at both the post-transcriptional level or the pre-transcriptional level. In a non-limiting example, epigenetic regulation of gene expression by siNA molecules of the invention can result from siNA mediated modification of chromatin structure and thereby alter gene expression (see, for example, Allshire (2002) *Science* 297, 1818-1819; Volpe et al. (2002) *Science* 297, 1833-1837; Jenuwein (2002) *Science* 297, 2215-2218; and Hall et al. (2002) *Science* 297, 2232-2237.)

An siNA can be designed to target any region of the coding or non-coding sequence of an mRNA. An siNA is a double-stranded polynucleotide molecule comprising self-complementary sense and antisense regions, wherein the antisense region comprises nucleotide sequence that is complementary to nucleotide sequence in a target nucleic acid molecule or a portion thereof and the sense region has a nucleotide sequence corresponding to the target nucleic acid sequence or a portion thereof. The siNA can be assembled from two separate oligonucleotides, where one strand is the sense strand and the other is the antisense strand, wherein the antisense and sense strands are self-complementary. The siNA can be assembled from a single oligonucleotide, where the self-complementary sense and antisense regions of the siNA are linked by means of a nucleic acid based or non-nucleic acid-based linker(s). The siNA can be a polynucleotide with a hairpin secondary structure, having self-complementary sense and antisense regions. The siNA can be a circular single-stranded polynucleotide having two or more loop structures and a stem comprising self-complementary sense and antisense regions, wherein the circular polynucleotide can be processed either in vivo or in vitro to generate an active siNA molecule capable of mediating RNAi. The siNA can also comprise a single stranded polynucleotide having nucleotide sequence complementary to nucleotide sequence in a target nucleic acid molecule or a portion thereof (or can be an siNA molecule that does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al. (2002) *Cell* 110, 563-574 and Schwarz et al. (2002) *Molecular Cell* 10, 537-568), or 5',3'-diphosphate.

In certain embodiments, the siNA molecule of the invention comprises separate sense and antisense sequences or regions, wherein the sense and antisense regions are covalently linked by nucleotide or non-nucleotide linkers molecules as is known in the art, or are alternately non-covalently linked by ionic interactions, hydrogen bonding, Van der Waal's interactions, hydrophobic interactions, and/or stacking interactions. Some preferred siRNAs are discussed in the Examples.

As used herein, siNA molecules need not be limited to those molecules containing oily RNA, but further encompasses chemically-modified nucleotides and non-nucleotides. In certain embodiments, the short interfering nucleic acid molecules of the invention lack 2'-hydroxy (2'-OH) containing nucleotides. In certain embodiments, short interfering nucleic acids do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached oar associated groups, moieties, or chains containing one or more nucleotides with 2'-OH groups. Optionally, siNA molecules can comprise ribonucleotides at about 5, 10, 20, 30, 40, or 50% of the nucleotide positions. The modified short interfering nucleic acid molecules of the invention can also be referred to as short interfering modified oligonucleotides "siMON." Other chemical modifications, e.g., as described in PCT/US03/05346 and PCT/US03/05028, can be applied to any siNA sequence of the invention.

Preferably a molecule mediating RNAi has a 2 nucleotide 3' overhang. If the RNAi molecule is expressed in a cell from a construct, for example from a hairpin molecule or from an inverted repeat of the desired sequence, then the endogenous cellular machinery will create the overhangs.

Considerations to be taken into account when designing an RNAi molecule include, e.g., the sequence to be targeted, secondary structure of the RNA target and binding of RNA binding proteins. Methods of optimizing siRNA sequences will be evident to the skilled worker. Typical algorithms and methods are described in Vickers et al. (2003) *J Biol Chem* 278:7108-7118; Yang et al. (2003) *Proc Natl Acad Sci USA* 99:9942-9947; Far et al. (2003) *Nuc. Acids Res.* 31:4417-4424; and Reynolds et al. (2004) *Nature Biotechnology* 22:326-330.

Methods of making siRNAs are conventional. In vitro methods include processing the polyribonucleotide sequence in a cell-free system (e.g., digesting long dsRNAs with RNAse III or Dicer), transcribing recombinant double stranded DNA in vitro, and, preferably, chemical synthesis of nucleotide sequences homologous to cMet sequence. See, e.g., Tuschl et al. (1999) *Genes & Dev.* 13:3191-3197.

In vivo methods include (1) transfecting DNA vectors into a cell such that a substrate is converted into siRNA in vivo. See, for example, Kawasaki et al. (2003) *Nucleic Acids Res* 31:700-707; Miyagishi et al. (2003) *Nature Biotechnol* 20:497-500; Lee et al. (2002) *Nature Biotechnol* 20:500-505: Brummelkamp et al. (2002) *Science* 296:550-553; McManus et al. (2002) *RNA* 8:842-850; Paddison et al. (2002) *Gene Dev* 16:948-958; Paddison et al. (2002) *Proc Natl Acad Sci USA* 99:1443-1448); Paul et al. (2002) *Nature Biotechnol* 20:505-508; Sui et al. (2002) *Proc Natl Acad Sci USA* 99:5515-5520; Yu et al. 2002) *Proc Natl Acad Sci USA* 99:6047-6052];

(2) expressing short hairpin RNAs from plasmid systems using RNA polymerase III (pol III) promoters. See, for example, Kawasaki et al., supra; Miyagishi et al., supra; Lee et al., supra; Brummelkamp et al., supra; McManus et al., supra), Paddison et al., supra (both); Paul et al., supra, Sui et al., supra; and Yu et al., supra; and/or (3) expressing short RNA from tandem promoters. See, for example, Miyagishi et al., supra; Lee et al., supra).

When synthesized in vitro, a typical µM scale RNA synthesis provides about 1 mg of siRNA, which is sufficient for about 1000 transfection experiments using a 24-well tissue culture plate format. In general, to inhibit cMet expression in cells in culture, one or more siRNAs can be added to cells in culture media, typically at about 1 ng/ml to about 10 µg siRNA/ml.

For reviews and more general description of inhibitory RNAs, see Lau et al. (2003 Aug) *Sci Amer* pp 34-41; McManus et al. (2002) *Nature Rev Genetics* 3, 737-747; and Dykxhoorn et al. (2003) *Nature Rev Mol Cell Bio* 4: 457-467.

For further guidance regarding methods of designing and preparing siRNAs, testing them for efficacy, and using them in methods of RNA interference (both in vitro and in vivo), see, e.g., Allshire (2002) *Science* 297:1818-1819; Volpe et al. (2002) *Science* 297:1833-1837; Jenuwein (2002) *Science* 297:2215-2218; Hall et al. (2002) *Science* 297 2232-2237; Hutvagner et al. (2002) *Science* 297:2056-60; McManus et al. (2002) *RNA* 8:842-850; Reinhart et al. (2002) *Genes Dev.* 16:1616-1626; Reinhart et al. (2002) *Science* 297:1831; Fire et al. (1998) *Nature* 391:806-811: Moss (2001) *Curr Biol* 11:R772-5:Brummelkamp et al. (2002) *Science* 296:550-553; Bass (2001) *Nature* 411 428-429; and Elbashir et al. (2001) *Nature* 411:494-498; U.S. Pat. No. 6,506,559; Published US Pat App. 20030206887; and PCT applications WO99/07409, WO99/32619, WO 00/01846, WO 00/44914, WO00/44895, WO01/29058, WO01/36646, WO01/75164, WO01/92513, WO 01/29058, WO01/89304, WO01/90401, WO02/16620, and WO02/29858.

Ribozymes and siNAs can take any of the forms, including modified versions, described for antisense nucleic acid molecules; and they can be introduced into cells as oligonucleotides (single or double stranded), or in an expression vector.

In a preferred embodiment, an antisense nucleic acid, siNA (e.g., siRNA) or ribozyme comprises a single stranded polynucleotide comprising a sequence that is at least about 90% (e.g., at least about 93%, 95%, 97%, 98% or 99%) identical to a segment of SEQ ID NO: 1, or 3, or a complement thereof. As used herein, a DNA and an RNA encoded by it are said to contain the same "sequence," taking into account that the thymine bases in DNA are replaced by uracil bases in RNA.

Active variants (e.g., length variants, including fragments; and sequence variants) of the nucleic acid-based inhibitors discussed herein are included. An "active" variant is one that retains an activity of the inhibitor from which it is derived (preferably the ability to inhibit expression). It is routine to test a variant to determine for its activity using conventional procedures.

As for length variants, an antisense nucleic acid or siRNA may be of any length that is effective for inhibition of a gene of interest. Typically, an antisense nucleic acid is between about 6 and abort 50 nucleotides (e.g., at least about 12, 15, 20, 25, 30, 35, 40, 45 or 50 nt), and may be as long as about 100 to about 200 nucleotides or more. Antisense nucleic acids having about the same length as the gene or coding sequence to be inhibited may be used. When referring to length, the terms bases and base pairs (bp) are used interchangeably, and will be understood to correspond to single stranded (ss) and double stranded (ds) nucleic acids. The length of an effective siNA is generally between about 15 bp and about 29 bp in length, preferably between about 19 and about 29 bp (e.g., about 15, 17, 19, 21, 23, 25, 27 or 29 bp), with shorter and longer sequences being acceptable. Generally, siNAs are shorter than about 30 bases to prevent eliciting interferon effects. For example, an active variant of an siRNA having, for one of its strands, the 19 nucleotide sequence of any of SEQ ID NO: 9-15 herein can lack base pairs from either, or both, of ends of the dsRNA; or can comprise additional base pairs at either, or both, ends of the ds RNA, provided that the total of length of the siRNA is between about 19 and about 29 bp, inclusive. One embodiment of the invention is an siRNA that "consists essentially of" sequences represented by SEQ ID NO: 9-15 or complements of these sequence. The term "consists essentially of" is an intermediate transitional phrase, and in this case excludes, for example, sequences that are long enough to induce a significant interferon response. An siRNA of the invention may consist essentially of between about 19 and about 29 bp in length.

As for sequence variants, it is generally preferred that an inhibitory nucleic acid, whether are antisense molecule, a ribozyme (the recognition sequences), or an siNA, comprise a strand that is complementary (100% identical in sequence) to a sequence of a gene that it is designed to inhibit. However, 100% sequence identity is not required to practice the present invention. Thus, the invention has the advantage of being able to tolerate naturally occurring sequence variations, for example, in human c-met, that might be expected due to genetic mutation, polymorphism, or evolutionary divergence. Alternatively, the variant sequences may be artificially generated. Nucleic acid sequences with small insertions, deletions, or single point mutations relative to the target sequence can be effective inhibitors.

The degree of sequence identity may be optimized by sequence comparison and alignment algorithms well-known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). At least about 90% sequence identity is preferred (e.g., at least about 92%, 95%, 98% or 99%), or even 100% sequence identity, between the inhibitory nucleic acid and the targeted sequence of targeted gene.

Alternatively, an active variant of an inhibitory nucleic acid of the invention is one that hybridizes to the sequence it is intended to inhibit under conditions of high stringency. For example, the duplex region of an siRNA may be defined functionally as a nucleotide sequence that is capable of hybridizing with a portion of the target gene transcript under high stringency conditions (e.g., 400 mM NaCl, 40 mM PIPES pH 6.4, 1 mM EDTA, 50° C. or 70° C., hybridization for 12-16 hours), followed generally by washing.

Murine DA3 cells, when not infected with the viral vector of the invention, respond to HGF stimulation by scattering. In contrast, the same cells infected with a viral vector comprising the present siRNA sequences do not respond, or respond more weakly, to HGF.

Met+ tumor cells infected with the siRNA vectors of the present invention have significantly reduced proliferative and invasive activity, and undergo enhanced apoptotic cell death. Infection with a viral vector comprising the siRNA of the present invention results in inhibition of phosphorylation of Met and its downstream pathways, manifest as reduced phosphorylation of Akt and p44/42 MAPK.

Delivery and expression of the siRNA compositions of the present invention inhibit (a) in vivo tumorigenesis de novo, and (b) growth of existing Met+tumor/cancer cells. These capabilities have been exemplified by showing that DA3 cells infected with si-mMet-Ad5[178] adenovirus in vitro and inoculated into mice sc are inhibited in their ability to form tumors. Moreover, treatment of subjects with si-met-Ad5[178] adenovirus resulted in a dramatic reduction in the tumor size. Thus the constructs of the present invention are useful for "nucleic acid" or "gene" therapy of Met-expressing cancer in vivo.

Therapeutic Compositions and Methods

The preferred animal subject of the present invention is a mammal. The invention is particularly useful in the treatment of human subjects. By the term "treating" is intended the administering to a subject of an effective dose of a pharmaceutical composition comprising an c-met siRNA or other c-Met specific siNA, preferably in the form of a viral vector that comprises (a) an expression construct of the siRNA operatively linked to a promoter, and (b) a pharmaceutically acceptable excipient or carrier. Preferred doses are between about 1 ng and 100 mg/kg body weight and may be administered once or repeatedly. The composition such as the viral vector, may be administered by any acceptable route, e.g. injected or infused systemically (preferably intravenously or intramuscularly), injected or instilled regionally, (e.g., subcutaneously, intrabronchially) or locally (e.g., intradermally, intrathecally). One preferred route is direct intratumoral administration.

The invention further relates to use of the c-met siRNA, other c-Met specific siNA, c-Met specific siNA expression constructs and viral vectors comprising such expression constructs for the manufacture of medicaments for use in therapeutic methods as herein described.

Having now generally described the invention, the same will be more readily understood through reference to the following examples which are provided by way of illustration, and are not intended to be limiting of the present invention, unless specified.

EXAMPLE 1

Materials and Methods

Cell lines. DA3 cells (poorly differentiated mouse mammary adenocarcinoma) (Firon et al, supra), M114 cells (NIH3T3 cells stably-transfected with mouse met and mouse HGF/SF), SK-LMS-1 human leiomyosarcoma cells (Zhang et al., supra), PC-3 human prostate cancer cells (Humphrey, P A et al., *Am J Pathol* 147:386-396, 1995), DBTRG human glioblastoma cells (Koochekpour, S et al., *Canc Res* 57:5391-5398, 1997), Madin-Darby canine kidney epithelial cells (MDCK) and TR6LM canine prostate carcinoma cells of a line established from a spontaneous lung metastasis, were grown in DMEM (Gibco™, Invitrogen Cooperation) supplemented with 10% heat-inactivated fetal bovine serum (FBS) (HyClone). Ovarian cancer cell lines CAOV3, ES2, and OVMZ6 (Munich) were similarly grown and the SKOV-3 line was maintained in suspension culture. MKN45 human gastric cancer cells (Kitamura, S et al., *Biochem Biophys Res Commun* 265:453-456, 1999) were grown in RPMI-1640 (Gibco™, Invitrogen Cooperation) supplemented with 10% FBS.

Met siRNA expression plasmids. The mU6 pro vector containing the mouse U6 promoter (Yu, J Y et al., *Proc Natl Acad Sci USA* 99:6047-6052, 2002) or the pSilencer 1.0-U6 siRNA expression vector (Ambion, Inc.) was used for the construction of mouse and human met siRNA expression plasmids. The siRNA target finder and design tool provided by Ambion, Inc. was used for selecting the siRNA sequences (see footnote). Four mouse and three human candidate siRNA sequences were selected from met mRNA sequences (Table 2). These sequences survived a BLAST search to ensure that there were no cross matches to other genes. The oligonucleotides that encode the Met mRNA 19-mer hairpin sequences were cloned into an expression vector plasmid (the BbsI and XbaI sites in the mU6 pro vector, and the ApaI and EcoRI sites in the pSilencer 1.0-U6 vector) and tested for Met suppression activity in either mouse or human cells, respectively.

Construction of c-met siRNA adenoviruses. The AdEasy™ Adenoviral Vector System (human adenovirus serotype 5, or Ad5, by Stratagene) was used. First, the selected siRNA sequences were recloned with the U6 promoter into a pShuttle vector. As a mock vector, U6 promoter without the siRNA sequence was used. Then, pShuttle vectors containing siRNA sequences were linearized with PmeI and cotransformed with pAdEasy-1 into BJ5183 cells by electroporation. Positive (homologously recombined) clones were selected and confirmed by PacI digestion. Plasmids with the correct insert were transformed into TOP10 competent cells and amplified; plasmid DNA was extracted using a QIAGEN Plasmid Midi Kit. The linearized adenoviral DNA was prepared by digesting the plasmid with PacI, after which it was transfected into the packaging cell line HEK293. Transfected cells were cultured for 7 d and the virus was harvested. After repeating one more amplification cycle, a large-scale amplification was performed by using a large-scale-production tissue culture plate (Cell Factory, Nunclon). Purification of the virus was performed according to Herz et al., *Proc Natl Acad Sci USA* 90:2812-2816, 1993. The virus titer was evaluated by plaque assay or end-point dilution.

Adenovirus infection. Cells at 75-80% confluence were exposed to c-met siRNA adenovirus diluted in a small volume of growth medium (+10% FBS) at a multiplicity of infection (moi) of 10 to 100 for 4 h at 37° C. After 4 h, fresh complete growth medium was added and the cells were cultured in a $CO_2$ incubator at 37° C. After 2 to 4 days in culture, the infected cells were collected for Western blotting, proliferation assays, invasion assays, or morphological analyses.

Western blot analysis. Cell extracts were separated by SDS-PAGE and transferred to PVDF membranes (Invitrogen). The membranes were incubated with antibodies against Met (SP260: sc-162, Santa Cruz; C-28: sc-161, Santa Cruz); phospho-Met ($Tyr^{1234/1235}$ rabbit polyclonal antibodies, Cell Signaling); p44/42 MAPK (rabbit polyclonal antibodies, Cell Signaling); phospho-p44/42 MAPK ($Thr^{202}/Tyr^{204}$ rabbit polyclonal antibodies, Cell Signaling); phospho-Akt ($Ser^{473}$, 587F11, Cell Signaling); or β-actin (AC-15: ab6276, abcam), followed by HRP-conjugated secondary antibodies (Santa Cruz). After incubation with ECL reagent (Amersham Biosciences), chemiluminescence signals were photographed and quantitated by image analysis.

Reverse transcription-polymerase chain reaction (RT-PCR) analysis. Total RNA was isolated using TRIzol reagent (Invitrogen). Reverse transcription was performed using 1 μg RNA and the SuperScript™ II RNase H⁻ Reverse Transcriptase (Invitrogen). One microliter of the RT product was used for amplification of c-met or β-actin genes. The primers used were

```
met-sense,
5'-AGCCAGTAATGATCTCAATAG-3';      (SEQ ID NO:5)

met-antisense,
5'-TCAGGATAGGGGACAGGT-3';         (SEQ ID NO:6)

β-actin sense,
5'-CGTGACATCAAAGAGAAGCTGTG-3';    (SEQ ID NO:7)
and

β-actin antisense,
5'-GCTCAGGAGGAGCAATGATCTTGA-3'.   ((SEQ ID NO:8)
```

The PCR conditions were 95° C. for 5 min, followed by 35 cycles of 95° C., 1 min; 55° C., 1 min; and 72° C., 1 min. The final extension was 72° C. for 5 min. Values were quantified using Scion image software and normalized to β-actin.

Scatter assay. Cells were seeded into six-well culture plates and treated with low-serum DMEM for 24 h (Stoker, M et al., *Nature* 327:239-242, 1987). Then assay medium containing HGF/SF (100 ng/ml) was added to the cells and they were incubated overnight. Cell scattering was observed microscopically.

Terminal deoxynucleotidyl transferase (TdT)-mediated dUTP nick end-labeling (TUNEL) assay. In Situ Cell Death Detection Kit, POD (Roche Diagnostics GmbH, Germany) was used for the TUNEL technology. Cells (1000/well) were seeded into 96-well microplates. After adhering, cells were infected with mU6-Ad5 mock or Met siRNA viruses at moi of 10, 50, and 100. Three and six days after infection, cells were fixed with 4% buffered formalin and processed for TUNEL assay according to manufacturer's instructions. Briefly, intrinsic peroxidase was blocked with 3% $H_2O_2$ in methanol for 10 min, and cells were permeabilized with 0.1% Triton X-100 in 0.1% sodium citrate. TdT reaction was performed for 60 min at 37° C. in a humidified atmosphere. Peroxidase substrate kit DAB (Vector Laboratories, Inc., CA) was used for the color development. Morphological evaluations were by light microscopy.

Sub-$G_1$ fraction analysis. Cells ($5\times10^4$/well) were seeded into 6-well plates and infected with Met siRNA viruses at different moi (10, 50, and 100). Three and six days after infection, cells were harvested and processed for flow cytometric analysis. The suspensions of tumor cells were prepared using the detergent-trypsin method (Vindelov et al., *Cytometry* 3:323-327, 1983) and stained with propidium iodide. Measurement of DNA cellular contents was performed with a flow cytometer (Becton-Dickinson). Fractions with DNA content below the 2C peak (sub-$G_1$ fraction) were calculated using the CELLQuest software package, and taken as apoptotic fractions.

In vitro invasion. Invasion assays were performed using a 24-well Matrigel™ invasion chamber plates (Becton-Dickinson) (Jeffers, M et al., *Mol Cell Biol* 16:1115-1125, 1996). Cells infected with Met siRNA adenovirus for three days were tested. Lower and upper wells were separated by 8 µm pore filters coated with Matrigel. In the lower wells was placed 0.75 ml 0.1% BSA-DMEM with or without HGF (100 ng/ml). Cells ($2.5\times10^4$) suspended in 0.5 ml 0.1% BSA-DMEM were placed in the upper wells and plates were incubated for 24 h in a $CO_2$ incubator. Non-invading cells in the upper wells were removed with cotton swabs and invading cells that migrated to the lower surface of the filter were fixed with methanol and stained with Diff-Quik® stain. The number of infiltrating cells was counted under a microscope.

Cell proliferation assay. Cells (1000/well) were seeded into 96-well microplates. After adhering, cells were infected with mU6-Ad5 mock or Met siRNA viruses at moi of 10, 50, and 100 and incubated for 2 days. Thereafter, cells were washed and the medium replaced with 0.1% BSA DMEM without FBS and incubated one more day. The cells were stimulated with HGF/SF (100 ng/ml) and incubated for 24 h. after which 10 µl of MTT (3-(4,5-dimethylthiazol-2-yl)-2,5-diphenyltetrazolium bromide; Sigma) were added to the wells and the plates incubated for 4 h. Subsequently, medium was removed and the produced dye was dissolved in 100 µl of DMSO. The formazan reaction product was determined with an ELISA plate reader (at a wavelength of 540 nm.

In vivo tumor formation. DA3 cells were infected with met siRNA adenovirus at moi of 100. Three days later, the cells were trypsinized, washed twice, and resuspended in Hanks' balanced salt solution (HBSS) supplemented with 0.6% lactalbumin hydrolysate. Cells, 105 in 0.1 ml HBSS, were injected sc into the right flank of BALB/c mice. Tumor formation was monitored twice weekly.

Activity of c-met siRNA adenovirus in vivo. DA3 cells (105) were inoculated sc into the right flank of BALB/c mice. After 3 and 7 days, c-met siRNA adenovirus ($4\times10^7$ infectious unit in 0.1 ml) was injected directly into the tumor. Tumor size was followed for 24 days. The mean and SD were calculated for each group, and statistical significance was evaluated using Student's t-test.

EXAMPLE 2 c-met siRNA Adenoviruses and Met Expression

Figure 1A:
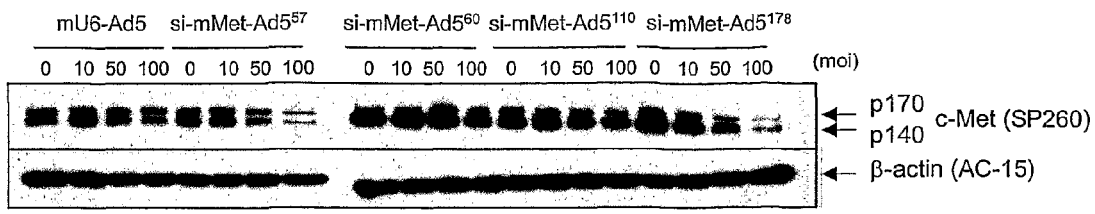
FIGS. 1A-1D show effect of c-met siRNA adenovirus infection on Met expression in tumor cells.

Four c-met siRNA adenoviruses were produced for mouse cells and three for human cells and three for canine cells (Table 2). In addition, mock viruses were prepared containing the mU6 promoter but no siRNA sequence (mU6-Ad5). M114 mouse NIH3T3 cells transformed with mouse met and HGF/SF (Rong, S et al., *Mol Cell Biol* 12:5152-5158, 1992) were used. The cells were infected with four different mouse c-met siRNA adenovirus preparations (si-mMet-Ad5$^{57, 60, 110, and 178}$; see Table 2) at moi=10, 50, and 100. Met expression was determined on 3 days after infection by Western blot (FIG. 1A). The expression of Met protein was dramatically suppressed by si-mMet-Ad5$^{57}$ and si-mMet-Ad5$^{178}$ at moi=50 and 100; mU6-Ad5 infected cells showed no effect on Met expression. Since M114 cells produce a high level of Met, both the p140 (mature) and p 170 (pro-form) Met were observed. The si-mMet-Ad5 adenoviruses reduced the quantity of both p140 and p170 Met proteins.

TABLE 2

Design of c-met siRNA adenovirus constructs

| Species | Adenovirus construct | siRNA gene position in c-met mRNA | 19-mer Target sequence | SEQ ID NO: |
|---|---|---|---|---|
| Mouse | si-mMet-Ad5$^{57}$ | 950 | GCCGCGTATGTCAGTAAAC | 9 |
|  | si-mMet-Ad5$^{60}$ | 988 | GCAAATAGGAGCTAGCCCT | 10 |
|  | si-mMet-Ad5$^{110}$ | 1839 | GCGAGAGCACGACAAATAC | 11 |
|  | si-mMet-Ad5$^{178}$ | 2762 | GTGATCGTTCAACCGGATC | 12 |
| Human | si-hMet-Ad5$^{16}$ | 415 | GACCTTCAGAAGGTTGCTG | 13 |
|  | si-hMet-Ad5$^{62}$ | 1236 | GCCAGATTCTGCCGAACCA | 14 |
|  | si-hMet-Ad5$^{221}$ | 3310 | GTGCAGTATCCTCTGACAG | 15 |

TABLE 2-continued

Design of c-met siRNA adenovirus constructs

| Species | Adenovirus construct | siRNA gene position in c-met mRNA | 19-mer Target sequence | SEQ ID NO: |
|---|---|---|---|---|
| Dog | si-dMet-Ad5[111] | 1904 | GTGAGAGCACAACAAATAT | 16 |
| | si-dMet-Ad5[197] | 2827 | GTAATAGTTCAACCAGATC | 17 |
| | si-dMet-Ad5[222] | 3130 | GTACAATATCCTCTGACGG | 18 |
| control | mU6-Ad5 (mock) | — | — | |

Figure 1B:
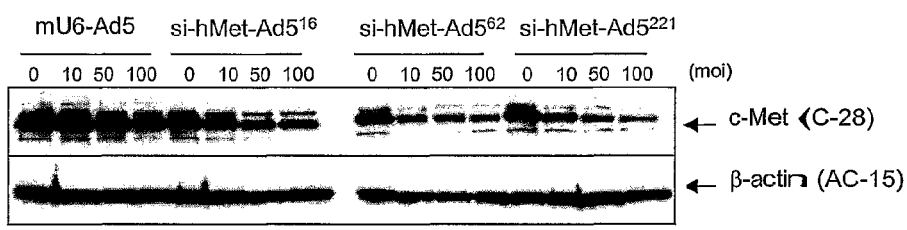
Figure 1C:
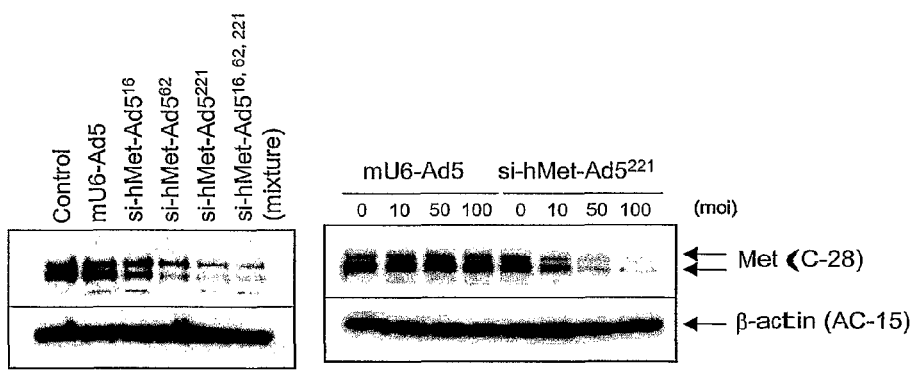
Figure 1D:
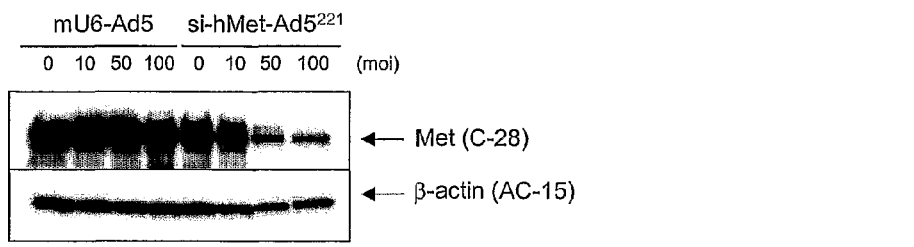

The effect of human c-met siRNA adenoviruses (si-hMet-Ad5[16, 62, and 221]) were tested on DBTRG human glioblastoma cells, PC-3 prostate cancer cells, and MKN45 human gastric cancer cells. All these cell lines express high levels of Met protein. Met expression was markedly suppressed by all three si-hMet-Ad5 forms at moi=10 to 100 (FIGS. 1B and 1C). The inhibitory effect was strongest with si-hMet-Ad5[221]. Met is constitutively activated in PC-3 cells and all three forms of si-hMet Ad5 significantly suppressed Met expression. When PC-3 cells were exposed to a mixture of all three forms (si-hMet-Ad5[16, 62, 221]) at 33.3 moi each, the RNAi effect was similar to the effect observed with si-hMet-Ad5[221] alone at 100 moi (FIG. 1C left). MKN45 cells express extremely high levels of Met, and, again, Met expression was dramatically suppressed by si-hMet-Ad5[221] at moi=50 or 100 (FIG. 1D). The effect of infection with si-hMet-Ad5[221] was tested on four human ovarian carcinoma cell lines: CAOV3, ES-2, SKOV-3 and OVMZ6 (Munich). Results shown in FIGS. 11A-11D indicate that Met expression was markedly reduced in ES-2 and SKOV-3, and even more dramtically suppressed in OVMZ6. Thus these inhibitory effects of Met-specific RNAi constructs are manifest on a variety of Met-expressing cancers of distinct tissue origin.

EXAMPLE 3

Effects of met RNAi on Cell Morphology

M114 cells are autocrine for HGF/SF and Met (Rong, S et al., Mol Cell Biol 12:5152-5158, 1992). Tests were done to determine whether suppression of Met expression and disruption of the autocrine loop would morphologically change the cells to a non-transformed appearance. After infection with si-mMet-Ad5 viruses, the M114 cells became less refractile and adhered tightly to the culture dishes (FIG. 2A, top), suggesting reversion to their NIH-3T3 (untransformed) phenotype. Non-infected control or mock virus-infected M114 cells retained spindle shapes and remained retractile. The RNAi effect on the M114 cell morphology is moi-dependent, and cell growth was significantly suppressed in si-mMet-Ad5[178]-infected cells at moi=50 or 100. The cells were more adherent and less refractile at higher moi (FIG. 2A, middle). Since cell density differed between the cells at different moi's, the cells were trypsinized and reseeded at a fixed concentration, and morphology was checked 24 h later. Again the M114 cells at moi=100 showed the most retractile and adherent appearance (FIG. 2A bottom).

Morphological change in DBTRG cells was more dramatic (FIG. 2B). Uninfected control cells revealed spindle shaped cell bodies and formed a multicellular palisade pattern. In contrast, si-hMet-Ad5[221]-infected cells showed a wider and rounder cytoplasm. Many cells lost their adherence and rounded up from the plate bottom at moi=50 to 100.

EXAMPLE 4

Specificity of Met Expression in DA3 Cells after Infection with si-mMet-Ad5

Figure 3A:
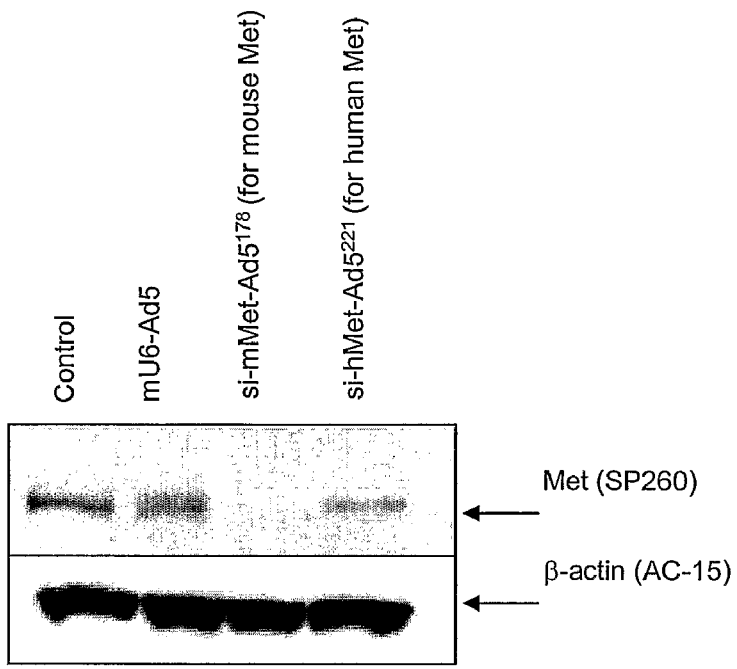
FIGS. 3A-3B.
Figure 3B:
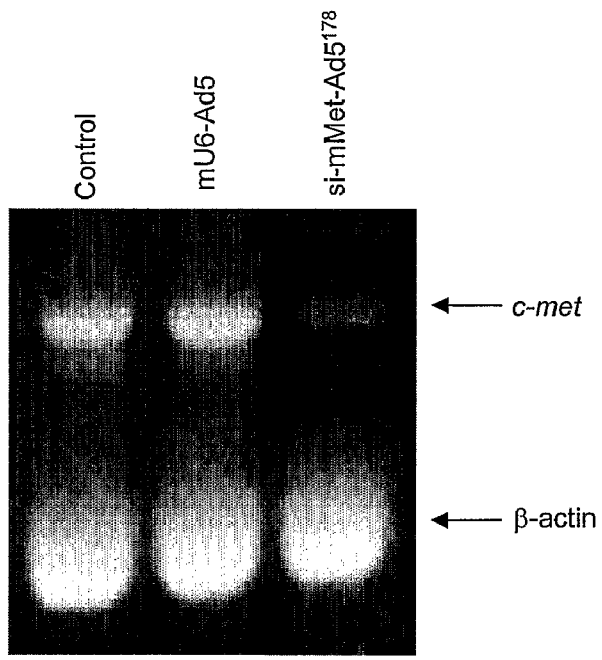

To test the specificity of the si-Met-Ad5 adenoviruses, DA3 mouse mammary adenocarcinoma cells were infected with siRNA adenoviruses specifically designed either for mouse Met (si-mMet-Ad5[178]) or for human Met (si-hMet-Ad5[221]), and the level of Met expression was observed at day 3 (FIG. 3A). Met expression was strongly suppressed only in the cells infected with si-mMet-Ad5[178] (although the si-hMet-Ad5[221] virus worked well in human cancer cell lines. See FIG. 1B, C, D. The effect of si-mMet-Ad5 adenovirus was also confirmed at the mRNA level by RT-PCR (FIG. 3B). A dramatic reduction in met mRNA expression was observed in DA3 cells infected with si-mMet-Ad5[178] virus. In contrast, no reduction in met mRNA was observed in mock-infected cells (mU6-Ad5).

EXAMPLE 5

Effects of met RNAi on Cell Scattering

Figure 4A:
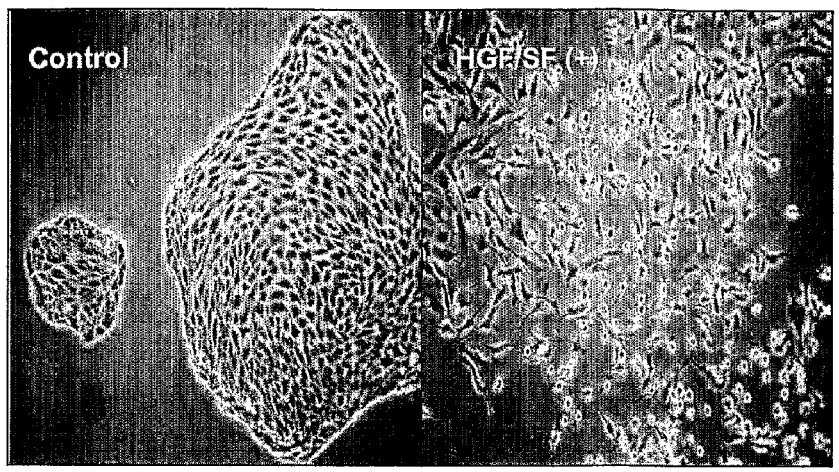
FIGS. 4A and 4B.
Figure 4B:
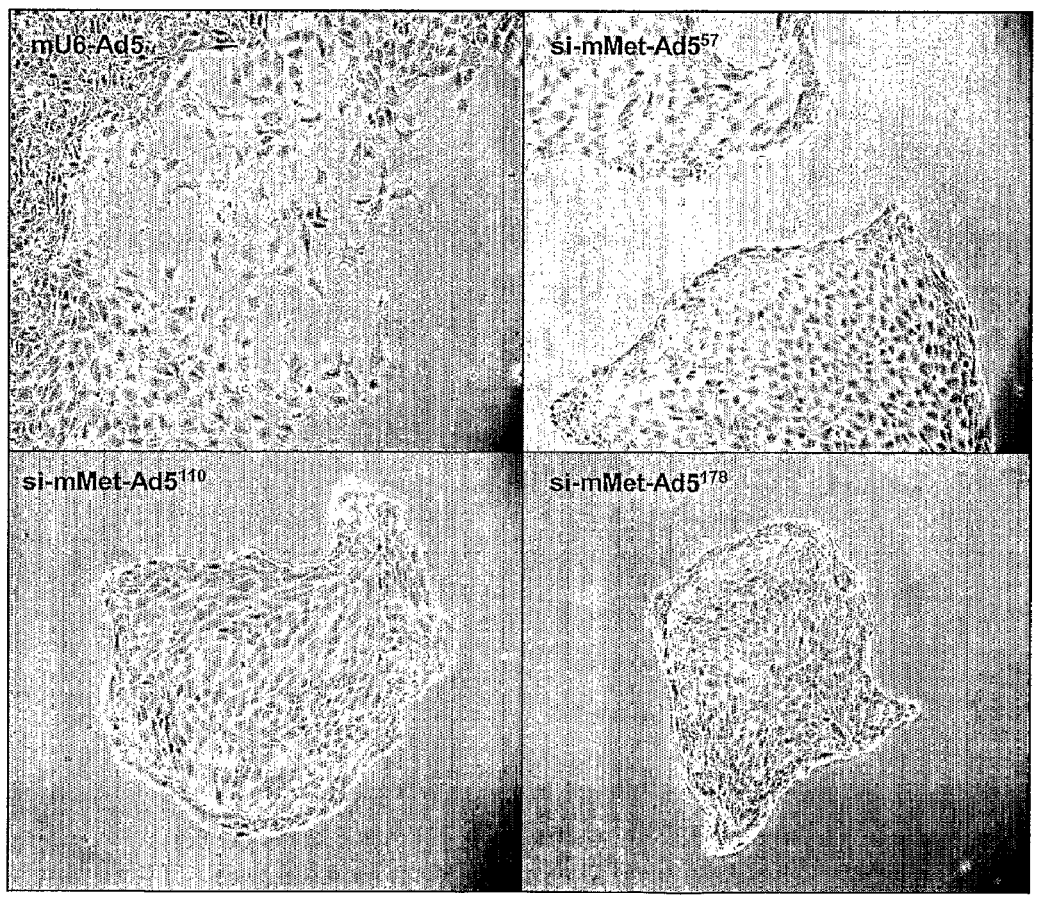

DA3 cells were tested for scattering activity in response to HGF/SF (Firon et al., supra) after infection with si-mMet-Ad5. Non-infected (control) DA3 cells showed dramatic scattering after HGF/SF stimulation (FIG. 4A) as did mock-infected cells. However, cell scattering was suppressed in all cells that were infected with si-mMet-Ad5 viruses 57, 110 and 178 (FIG. 4B).

EXAMPLE 6

RNAi Persistence after Cell Passage

Figure 5A:
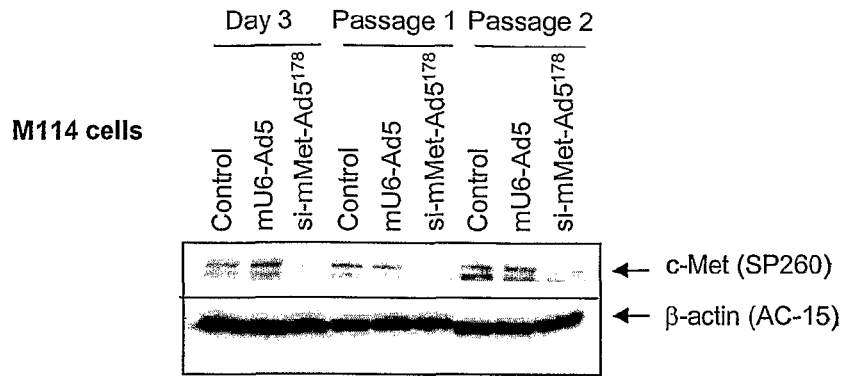
FIGS. 5A-5C show RNAi persistence after cell passage.

The inventors determined how long the RNAi effects continued after cell passage. M114 cells were infected with si-mMet-Ad5[178] at moi=100 and Met expression was determined at 3-d intervals for up to nine days (FIG. 5A). Three days after infection, p140 and p170 Met were dramatically suppressed (<5% expression) compared with non-infected or mock-infected cells. Cells were trypsinized and reseeded at lower concentration, and after culture for 3 d, Met expression remained strongly suppressed (passage 1, FIG. 5A). After another passage, Met expression was still markedly reduced but increased slightly vs. passage 1. These results suggest that not only is the Met expression suppressed in the primary infected cells, but the RNAi effect persists for several cell cycles.

Figure 5B:
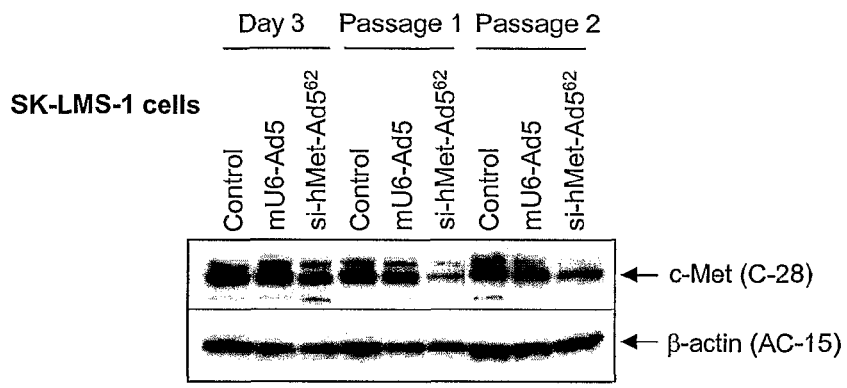

SK-LMS-1 cells were similarly tested and found to be refractory to si-hMet-Ad5 infection compared to other human cell lines. Met expression was not suppressed even at moi=100 at day 3. However, after cell passage Met expression was efficiently suppressed (FIG. 5B). Collectively, these results show that the RNAi lasts through multiple cell divisions.

Figure 5C:
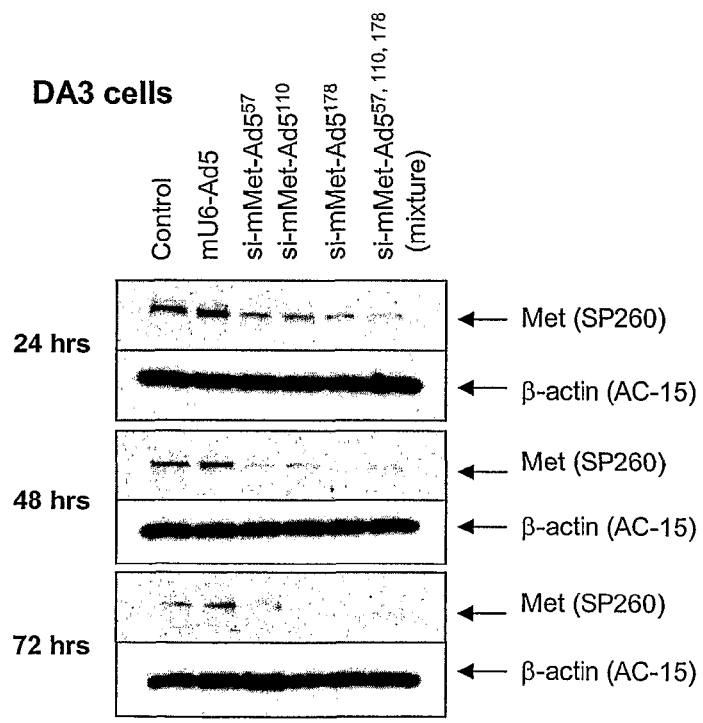

DA3 cells were infected with si-mMet-Ad5 viruses at moi=100 and Met expression was determined for 3 d (FIG. 5C). At 24 h, the Met expression decreased in all infected cell groups but not in control or mock virus (mU6-Ad5)-infected cells. At 48 and 72 h, Met reduction was more dramatic and in all cases was 25% or less relative to control cells. si-mMet-Ad5[178] was most effective, and by 72 h Met expression was nil. A mixture of the three, si-mMet-Ad5[57, 110, 178], was no more effective than si-mMet-Ad5[178] alone. Similarly, Met expression was tested in the DA3 cells after cell passage. RNAi lasted beyond one passage. However, the RNAi effect was so dramatic that the cells could not survive under the influence of the potent RNAi effect.

EXAMPLE 7

Met RNAi Induces Apoptotic Cell Death

Figure 6:
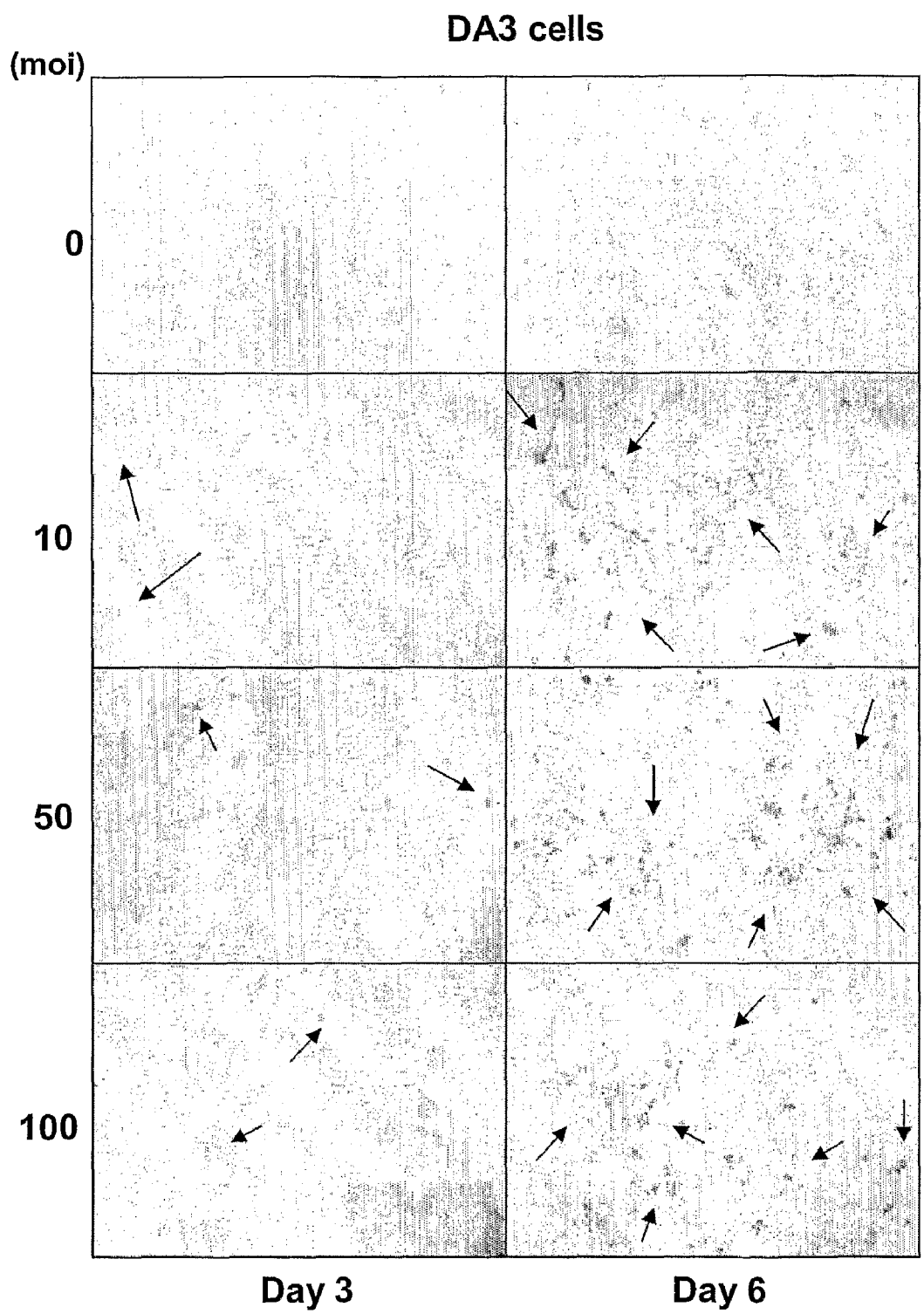
FIG. 6 shows results of a TUNEL assay of si-mMet-Ad5$^{178}$ adenovirus-infected DA3 cells. The DA3 cells were infected with si-mMet-Ad5$^{178}$ viruses at different moi (0, 10, 50, 100). Cells were fixed with formaldehyde at day 3 and 6, and apoptotic cells were detected by a TUNEL assay. Apoptotic cells are stained with dark brown (arrows). Three days after infection, suppression of cell growth is obvious at moi=50-100, and there are some apoptotic cells in si-mMet-Ad5$^{178}$ adenovirus-infected cells. At day 6, many apoptotic cells are detected at moi=10-100.

Because DA3 cells could not maintain viability after a second passage following infection with si-mMet-Ad5[178], the possibility that they underwent apoptotic cell death was tested. DA3 cells were infected with si-mMet-Ad5[178] at different moi (10, 50, and 100), and apoptotic changes were assessed by TUNEL assay (FIG. 6). Three days after infection, cell growth was suppressed dose-dependently, and darkly stained apoptotic cells were observed in the si-mMet-Ad5[178]-infected group. At day 6, the ratio of TUNEL-positive cells increased dramatically, and many apoptotic cells (>30 cells/high power field) were observed at moi=100. A similar but less pronounced apoptotic change was observed in MKN45 and PC-3 cells after infection with si-hMet-Ad5[221] (Table 3). Although the frequency was lower than these three cancer cell lines, DBTRG, SK-LMS-1, and SK-HGF cells also showed an apoptotic change. However, M114 cells (NIH-3T3 cells transformed with mouse met and HGF/SF), did not show an obvious increase in the TUNEL-positive cells, suggesting that Met expression is not essential in the survival of this cell line. Growth inhibition of Met siRNA adenovirus-infected cells seemed to correlate with the extent of apoptotic changes (Table 3). Interestingly, proliferation of SK-LMS-1-HGF cells was more strongly suppressed than that of SK-LMS-1 cells, suggesting that infection with si-Met-Ad5 virus effectively blocked the autocrine loop of HGF/SF-Met stimulation.

Figure 7:
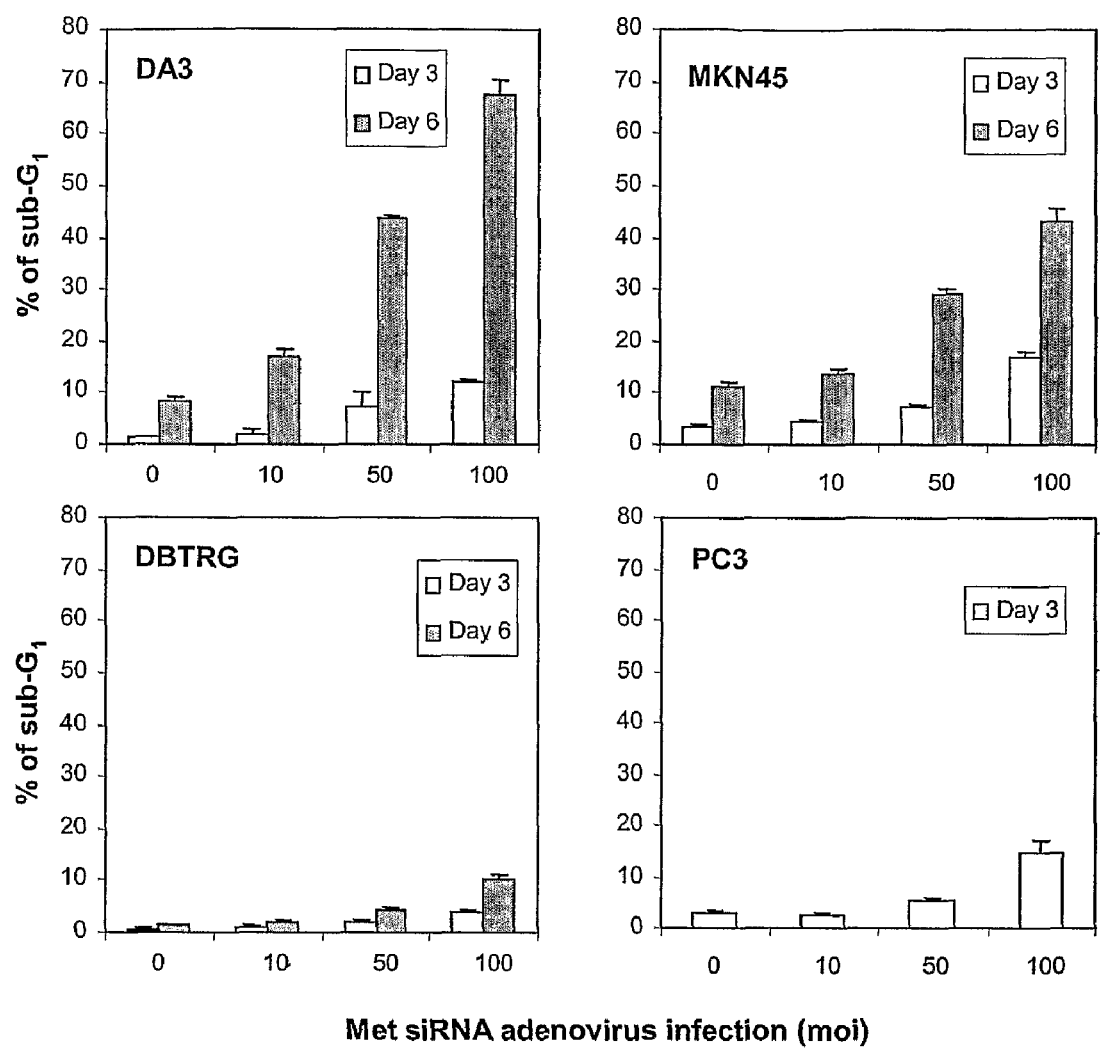
FIG. 7 shows quantitative analysis of apoptosis after infection with Met siRNA adenovirus. DA3, MKN45, DBTRG, and PC-3 cells were infected with si-Met-Ad5 viruses (si-mMet-Ad5$^{178}$ for DA3 and si-hMet-Ad5$^{221}$ for MKN45, DBTRG, and PC-3) at different moi's (0, 10, 50, 100). Three and six days after infection, both detached and adherent cells were collected and stained with propidium iodide (PI). The cells were analyzed by flow cytometry, and sub-G$_1$ fraction (i.e., apoptotic fraction) was calculated. Three days after infection, the cells began to become apoptotic at moi=50-100.

To quantitate apoptosis in Met siRNA adenovirus-infected cells, sub-$G_1$ fraction analysis was performed (FIG. 7). Apoptosis was induced in an infectious dose-dependent manner. Among the cell lines tested, DA3 cells were most susceptible to apoptosis and the sub-$G_1$ fraction 6 days after infection reached 67.3±3.2% at moi=100. There was no reduction in the viability of the DA3 cells infected with mock mU6-Ad5 virus at moi=100 at day 6. MKN45 cells were also sensitive to apoptosis and sub-$G_1$ ratio at moi=100 reached 43.1±2.7% at day 6 DBTRG cells were less susceptible to apoptosis than DA3, MKN45, and PC-3, but sub-$G_1$ fraction at moi=100 showed yet 10.4±0.5% and was significant when compared to non-infected control cells.

TABLE 3

Susceptibility to apoptosis, growth inhibition, and morphological changes after infection with Met siRNA adenovirus

| Cells | Apoptosis* | Growth inhibition** (cell confluence) | Morphological changes*** |
|---|---|---|---|
| DA3 | +++ | +++ | — |
| M114 | +/− | + | + (less refractile, flatter) |
| PC-3 | ++ | ++ | — |
| DBTRG | + | ++ | + (less spindly, rounder) |
| MKN45 | ++ | +++ | — |
| SK-LMS-1 | + | + | — |
| SK-HGF# | + | ++ | — |

*Frequency of apoptosis was evaluated by TUNEL assay. Cells were infected with Met siRNA adenovirus at moi = 100 and cultured for 6 days. +/−: <5 apoptotic cells/high power field; +: 5-10 apoptotic cells; ++: 11-30 apoptotic cells; +++: >30 apoptotic cells.
**$10^4$ cells were plated in 96-well plates and infected with Met siRNA adenovirus at moi = 100. Growth inhibition was estimated at day 3 after infection. Cell morphology was observed using phase contrast microscopy. All control cells reached confluence before day 3. +: confluent but cell density differs from control; ++: 60-70% confluent; +++: less than 50% confluent.
***Morphological changes were evaluated using phase contrast microscopy (see also FIG. 2).
SK-HGF cells are SK-LMS-1 cells that have been made autocrine for HGF/SF (Jeffers, 1996, supra)

EXAMPLE 8 met RNAi on TR6M Canine Prostate Carcinoma Cells and Nontransformed MDCK Cells

The effects of three different si-dMET-Ad5 viruses were tested at moi=50 and 100 on nontransformmed canine MDCK cells and TR6LM prostate carcinoma cells. All three viruses were very effective at knocking down Met expression in both MDCK and TR6LM cells (FIG. 10A). The order of Met suppression in MDCK was si-dMet-Ad5[111]>si-dMet-Ad5[222]>si-dMet-Ad5[197]. In TR6LM cells, Met expression was almost completely inhibited by each of the three siRNA constructs. The growth and viability of the TR6LM canine prostate cancer cells was adversely affected whereas the viability and proliferation of MDCK cells was not obviously affected (not shown). However, MDCK cell scattering was suppressed and the scattering response paralleled the level of Met reduction FIG. 10B, showing that reduction of Met expression can affect Met-dependent cell scattering without affecting cell viability or proliferation. Thus, si-dMet-Ad5[197]-infected MDCK cells scattered the most and expressed th highest level Met, whereas the si-dMet-Ad5[111]-infected cells scattered the least and expressed the lowest level of Met.

EXAMPLE 9 met RNAi Suppresses Signaling

HGF/SF binding to Met results in Met phosphorylation and activation of downstream pathways such as the phosphoinositide 3 kinase (PI3K)-Akt (Graziani, A et al., *J Biol Chem* 266:22087-22090, 1991) and the mitogen-activated protein (MAP) kinase pathways (Karihaloo, A et al., *J Biol Chem* 276:9166-9173, 2001). These pathways are essential for biological functions such as cell migration, proliferation, morphogenesis, and escape from apoptotic cell death.

After exposure to HGF/SF DA3 cells showed steady or increased level of Met phosphorylation for 2 h, followed by a gradual decrease (FIG. 8A) (Firon et al., supra). p44/42 MAPK and Alt were also rapidly phosphorylated 10 min after HGF/SF stimulation. In contrast, phosphorylation of p44/42

MAPK lasts longer in these cells. Endogenous phosphorylation of Met and p44/42 MAPK are observed in DA3 cells in the absence of HGF/SF stimulation (0 min) after serum starvation. This suggests that other signaling pathways are acting in these cells or Met activation is ligand-independent.

In non-infected control and mock virus (mU6-Ad5)-infected cells, Met was rapidly phosphorylated in response to HGF/SF. Increased phosphorylation of Akt and p44/42 MAPK was also observed. Although p44/42 MAPK phosphorylation was observed in si-mMetAd5$^{178}$-infected cells, it was significantly suppressed compared with non-infected controls and mock infected cells. However, the phosphorylation of Met and Akt was almost completely abolished (FIG. 8B). Since Akt activation contributes to the stimulation of an anti-apoptotic pathway, the reduced level of phospho-Alt is consistent with increased susceptibility of si-mMet Ad5$^{178}$-infected DA3 cells to apoptotic cell death.

EXAMPLE 10

Met RNAi Inhibits Cell Invasion and Proliferation In Vitro

The influence of si-Met-Ad5 virus infection on Met-mediated in vitro invasion by DA3 mouse mammary adenocarcinoma cells was tested. Infected or mock-infected DA3 cells were plated in Matrigel® chambers and invasion assays were performed after treatment with HGF/SF. Without HGF/SF stimulation, the cells did not migrate and only a few cells were detected by Giemsa staining. In response to HGF/SF, however, non-infected control DA3 cells readily invaded Matrigel®; approximately 80 cells wee detected per filter. In contrast, cells infected with met siRNA viruses showed markedly reduced invasion. Such activity was almost completely suppressed in the cells infected with si-mMet-Ad5$^{178}$ which was correlated with interference of Met expression (not shown).

Likewise, si-hMet-Ad5$^{221}$ dramatically suppressed invasion activity of human cancer cell lines. Cells of both PC-3 and SK-LMS-1 lines that are stably transfected with the human hgf/sf gene (SK-HGF) (Jeffers et al., supra) displayed reduced invasion (not shown). PC-3 and SK-HGF cells are less dependent on extrinsic HGF/SF than are other human cancer cell lines. These results show that invasive activity was largely dependent on Met signaling. Interestingly, PC-3 cells show little or no proliferative or invasive response to HGF/SF and express high levels of Met (Nishimura, K et al., *Int J Urol* 5:276-281, 1998). However, the loss of Met revealed an inhibitory effect on invasive activity, suggesting that Met signaling is autonomous (no mutation found) perhaps by ligand independent activation.

The effect of RNAi on DA3 cell proliferation was tested. As measured by the MTT assay, the growth response after stimulation with HGF/SF was strongly suppressed by si-mMet-Ad5$^{178}$ infection even at moi=10, and the suppressive effect peaked at moi=50. In contrast, mock mU6-Ad5 virus did not show any suppressive effect on cell growth at moi=10 to 50, and only mild suppression was observed at moi=100. These results suggested that met RNAi suppressed both invasion and proliferation, which are important for tumor cell progression.

EXAMPLE 11 met RNAi Suppresses Tumorigenesis met RNAi suppressed the expression of Met protein and blocked scattering, proliferation, and invasion as well as downstream signaling in vitro. Experiments were done to test whether si-Met-Ad5 RNAi would also suppress tumorigenicity. The first study tested whether DA3 cells infected with si-mMet-Ad5$^{178}$ which grow in vitro would also grow as tumors in BALB/c mice upon sc inoculation. Tumor growth was measured for 3 weeks, and a dramatic difference was observed. All mice (10/10) showed remarkable tumor growth when inoculated sc with uninfected "control" tumor cells. In contrast, tumor formation by DA3 cells infected with si-mMet-Ad5$^{178}$ was almost completely suppressed ($p<0.001$ vs. uninfected control; $p<0.01$ vs. mU6-Ad5) (FIG. 9A).

si-mMet-Ad5 was tested for suppression of tumor formation in vivo (siRNA gene therapy). DA3 cells were inoculated subcutaneously in the flank of BALB/c mice, and then si-mMet-Ad5$^{178}$ was injected directly into the tumor 3 and 7 d after tumor inoculation. The mice injected with si-mMet-Ad5$^{178}$ virus showed a statistically significant reduction in the tumor size ($p<0.05$ to $0.01$), whereas there was no remarkable difference in the tumor size between PBS control and mock virus (mU6-Ad5)-treated mice (FIG. 9B). This result supports the use RNAi for cancer treatment.

DISCUSSION OF EXAMPLES 1-11

RNAi is a potent tool for silencing the function of specific genes (Elbashir et al., supra). The present Examples involved production of siRNA adenoviruses that carry target sequences against either mouse or human Met. The different adenoviral constructs showed different, reproducible patterns of suppression of Met protein expression (see FIG. 1). For instance, the rank order of Met suppression in mouse cell lines (M114 and DA3) was si-mMet-Ad5$^{178}$>si-mMet-Ad5$^{110}$, si-mMet-Ad5$^{57}$>si-mMet-Ad5$^{60}$ (see FIGS. 1A and 5C). In human cell lines (DBTRG, and PC-3), the rank order was si-hMet-Ad5$^{221}$>si-hMet-Ad5$^{62}$>si-hMet-Ad5$^{16}$ (see FIGS. 1B and 1C). si-hMet-Ad5$^{221}$, which was the most potent in human cell lines, did not affect Met expression in mouse DA3 cells, whereas si-mMet-Ad5$^{178}$ produced a dramatic reduction in the Met protein level in those cells (see FIG. 3A). This effect was confirmed by evaluating mRNA levels (see FIG. 3B). These results show that the siRNA constructs of the present invention mediate RNAi effects in a sequence-specific manner.

The effective duration of RNA interference was examined. According to a previous report, silencing in dividing cells lasts only 3 to 7 d, presumably because of dilution of siRNA secondary to cell division (Song, E et al., *J Virol* 77:7174-7181, 2003). Here, the greatest effects were observed after the first cell passage (day 67 after infection); RNAi was still evident after passage 2 (see FIG. 5). This means that RNAi lasts at least 9-10 d after siRNA adenovirus infection. Because these adenoviral constructs include a U6 promoter-based RNA transcription system, there should be more siRNA molecules per cell compared with cells transfected directly with siRNA molecules. After si-mMet-Ad5 infection, RNAi was induced swiftly, and close to a 50% reduction in Met expression was observed by 24 h (see FIG. 5C); the effect of RNAi increased gradually by 72 h. This suggested that short hairpin RNA can be transcribed efficiently after the siRNA adenovirus genes are established in the cytoplasm.

The efficiency of Met reduction by si-Met-Ad5 varied among the cell lines. DBTRG, PC-3, and MKN45 cells (see FIG. 1) responded better than did SK-LMS-1, and the suppression of Met expression in DA3 cells was more robust than that in M114 cells (see FIGS. 1 and 5). Entry of adenovirus requires two receptors: a primary receptor known as the Coxsackievirus/adenovirus receptor (CAR) for attachment, and secondary receptors such as the $\alpha_v\beta_3$ and $\alpha_v\beta_5$ integrins for internalization (Nemerow, G R, *Virology* 274:1-4, 2000). Recent reports showed that loss of CAR expression was a major limiting factor in adenovirus gene therapy (Pearson, A S et al., *Clin Canc Res* 5:4208-4213, 1999). Since the cell lines of epithelial origin (DBTRG, PC-3, MKN45, and DA3) are considered to express higher levels of CAR than the non-epithelial lines (SK-LMS-1 and M114), the infectivity might explain the difference in Met reduction.

Abrogation of HGF/SF-Met signaling to suppress the Met-dependent malignant phenotype has been achieved by several different approaches. In one, a dominant-negative (DN) form of Met reduced in vitro motility and invasiveness as well as the in vivo tumorigenic and metastatic potential, of DA3 cells (Firon et al., supra)

Although the molecular mechanism of the DN-Met effect is not entirely clear, dimerization of the DN-Met receptor with the wild-type receptor is believed to interfere with HGF/SF-induced Met signaling. In the context of Met signaling, however, direct molecular targeting of the Met protein would be a more straightforward and robust way to test the mechanism. Abounader et al. (2002, supra) designed a U1snRNA/ribozyme for targeting Met and reported that it reversed the malignancy of glioma cells, inhibited the growth and angiogenesis, and promoted apoptosis. Targeted gene expression was inhibited effectively measured as mRNA and protein levels of 73-98% by using stable expression of U1snRNA/ribozyme. However, the efficiency of transient infection using an adenovirus system remained 75% reduction in mRNA and 50% reduction in Met protein. In contrast, the present si-Met-Ad5 system induced a more efficient reduction (confirmed by western blot analysis). Reduction in Met expression reached 62% in DBTRG cells, 68% in PC-3 cells, and 71% in MKN45 cells (see FIG. 1B, 1C, and 1D). In the more sensitive DA3 cell line, the reduction was between 85% and nearly 100% (see FIGS. 3A and 5C). Despite a variation in the susceptibility to si-Met-Ad5 viruses among the cell lines analyzed, the present RNAi system provides a higher certainty of Met reduction than do other known methods.

The RNAi effect mediated by si-Met-Ad5 not only by suppressed invasion and proliferation, but also promoted cell death. Despite the fact that Met expression levels did not necessarily correlate with susceptibility to apoptosis, a reduction in Met protein triggered more cell death in cancer cell lines such as DA3 and MKN45, and in several other cell lines (to a lesser extent) (see FIGS. 6 and 7, and Table 3). In contrast, M114 cells after si-Met-Ad5 infection underwent morphological changes without frank apoptosis (see Table 3), suggesting that Met expression is more important for survival of cancer cells than normal cells such as fibroblasts. Upon HGF/SF stimulation, the Met receptor is phosphorylated, followed by the recruitment of a group of signaling molecules and/or adaptor proteins to its cytoplasmic domain and multiple docking sites (Zhang, Y W et al., *J Cell Biochem* 88:408-417, 2003). This leads to activation of several different signaling cascades that form a unique network in various types of outward responses; such as cell proliferation, cell migration, cell invasion, angiogenesis, and metastasis.

After infection with si-mMet-Ad5, DA3 cells showed remarkable suppression of scattering (see FIG. 4B), invasion, and proliferation, and similar results were observed in human cell lines (PC-3 and SK-HGF). Marked suppression of the phosphorylation of Met and of downstream molecules (Akt and p44/42 MAPK) was observed in si-mMet-Ad5-infected DA3 cells (but not in mock-infected cells). See FIG. 8B. These findings suggests that all the phenotypic changes are effected by suppression of the phosphorylation of Met and downstream molecules. HGF/SF signaling is known to stimulate the Akt pathway and to protect cancer cells from death (Bowers, D C et al., *Canc Res* 60:4277-4283, 2000). HGF/Met can protect cells from apoptosis through both PI3-kinase/Akt and, to a lesser extent, MAPK pathways (Xiao et al., supra). Actually, the present results with DA3 cells infected with si-mMet-Ad5[178] showed a very low Akt response while generally maintaining a MAPK signaling pathway (see FIG. 8B). This suggests the importance of the Akt pathway for viability of DA3 cells.

Since overexpression or active mutation of the Met protein is involved in a wide spectrum of solid tumors, Met is considered one of the key targets for cancer gene therapy (Ma, P C et al., *Cancer Metastasis Rev* 22:309-325, 2003. Recently, in vivo treatment approaches that target the HGF/SF-Met signaling were reported by several groups. One approach used the NK4 gene that acts competitively with HGF/SF (Maemondo, M et al., *Mol Ther* 5:177-185, 2002). However, this therapy is limited to tumor cells in which Met signaling is ligand-dependent. Other reports disclosed DN-Met (Furge et al., supra) or Met ribozyme (Herynk, M. H et al., *Canc Res* 63:2990-2996, 2003) as targeting tools. Although these reports showed statistically significant suppression of tumor growth, there continues to be a need for improved genetic tools for more efficient anti-cancer activity.

This document provides the first disclosure that c-met siRNA adenovirus can effectively suppress Met expression and a wide variety of tumor functions, and that these effects could be manifest both in vitro (see FIGS. 2, 4, 6 and 7) and in vivo (see FIG. 9).

It was concluded that the si-Met-Ad5 adenovirus constructs provide a powerful tool for the analysis of the HGF/SF-Met signaling pathway, as well as cancer therapy, preferably in the form of cancer gene (or nucleic acid) therapy.

All the references cited above are incorporated herein by reference in their entirety, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. An interfering RNA (RNAi) molecule that is between about 19 and about 29 nucleotides in length and hybridizes to a Met target sequence comprising SEQ ID NO: 15.

2. The RNAi molecule of claim 1 that is a single stranded siRNA that forms a hairpin structure.

3. The RNAi molecule of claim 1 that is a double stranded siRNA.

4. A DNA molecule encoding the RNAi molecule of claim 1.

5. An expression construct comprising DNA that encodes the RNAi molecule of claim 1 operatively linked to a promoter that drives the expression of said RNAi molecule in a c-met-expressing cell.

6. An expression construct comprising the DNA molecule of claim 4.

7. The expression construct of claim 5, wherein the promoter drives the expression of said RNAi molecule in a c-met-expressing tumor or cancer cell.

8. The expression construct of claim 7 wherein the promoter is a polIII promoter.

9. The expression construct of claim 8 wherein the polIII promoter is a U6 promoter.

10. A viral vector comprising the expression construct of claim 5.

11. The viral vector of claim 10 that is a transient expression vector.

12. The viral vector of claim 10 that is a stable expression vector.

13. The viral vector of claim 10 that is an adenoviral vector.

14. The adenoviral vector of claim 13 that is an Ad5 viral vector.

15. A method of treating a c-met+ tumor or cancer in a subject, comprising administering to the subject by an effective route, an amount of the viral vector of claim 10 effective for inhibiting expression of c-met and thereby (i) inhibiting the growth, invasion or metastasis of cells of said tumor or cancer, or (ii) killing said tumor or cancer cells.

16. The method of claim 15 wherein the tumor or cancer is glioblastoma, prostate or gastric.

17. An interfering RNA (RNAi) molecule that is between about 19 and about 29 nucleotides in length and comprises the nucleotide sequence shown in SEQ ID NO: 15 wherein U is substituted for T.

18. A DNA molecule encoding the RNAi molecule of claim 17.

19. An expression construct comprising the DNA molecule of claim 18.

20. An expression construct comprising DNA that encodes the RNAi molecule of claim 18 operatively linked to a promoter that drives the expression of said RNAi molecule in a c-met-expressing cell.

21. A viral vector comprising the expression construct of claim 19.

22. The viral vector of claim 21 that is an adenoviral vector.

23. A method of treating a c-met+ tumor or cancer in a subject, comprising administering to the subject by an effective route, an amount of the viral vector of claim 21 effective for inhibiting expression of c-met and thereby (i) inhibiting the growth, invasion or metastasis of cells of said tumor or cancer, or (ii) killing said tumor or cancer cells.

24. The method of claim 23 wherein the tumor or cancer is glioblastoma, prostate or gastric.

* * * * *

SEQUENCE LISTING

<160> NUMBER OF SEQ ID NOS: 18

<210> SEQ ID NO 1
<211> LENGTH: 4620
<212> TYPE: DNA
<213> ORGANISM: Homo sapiens

<400> SEQUENCE: 1

```
cgccctcgcc gcccgcggcg ccccgagcgc tttgtgagca gatgcggagc cgagtggagg      60
gcgcgagcca gatgcgggc gacagctgac ttgctgagag gaggcgggga ggcgcggagc      120
gcgcgtgtgg tccttgcgcc gctgacttct ccactggttc ctgggcaccg aaagataaac     180
ctctcataat gaaggccccc gctgtgcttg cacctggcat cctcgtgctc ctgtttacct     240
tggtgcagag gagcaatggg gagtgtaaag aggcactagc aaagtccgag atgaatgtga     300
atatgaagta tcagcttccc aacttcaccg cggaaacacc catccagaat gtcattctac     360
atgagcatca cattttcctt ggtgccacta actacattta tgttttaaat gaggaagacc     420
ttcagaaggt tgctgagtac aagactgggc ctgtgctgga cacccagat tgtttcccat      480
gtcaggactg cagcagcaaa gccaatttat caggaggtgt ttggaaagat aacatcaaca     540
tggctctagt tgtcgacacc tactatgatg atcaactcat tagctgtggc agcgtcaaca     600
gagggacctg ccagcgacat gtctttcccc acaatcatac tgctgacata cagtcggagg     660
ttcactgcat attctcccca cagatagaag agcccagcca gtgtcctgac tgtgtggtga     720
gcgccctggg agccaaagtc ctttcatctg taaaggaccg gttcatcaac ttctttgtag     780
gcaataccat aaattcttct tatttcccag atcatccatt gcattcgata tcagtgagaa     840
ggctaaagga acgaaagat ggttttatgt ttttgacgga ccagtcctac attgatgttt      900
tacctgagtt cagagattct taccccatta agtatgtcca tgcctttgaa agcaacaatt     960
ttatttactt cttgacggtc caaagggaaa ctctagatgc tcagactttt cacacaagaa    1020
taatcaggtt ctgttccata aactctggat tgcattccta catggaaatg cctctggagt    1080
gtattctcac agaaaagaga aaaagagat ccacaaagaa ggaagtgttt aatatacttc     1140
aggctgcgta tgtcagcaag cctggggccc agcttgctag acaaatagga gccagcctga    1200
atgatgacat tctttttcggg gtgttcgcac aaagcaagcc agattctgcc gaaccaatgg    1260
atcgatctgc catgtgtgca ttccctatca aatatgtcaa cgacttcttc aacaagatcg    1320
tcaacaaaaa caatgtgaga tgtctccagc attttttacgg acccaatcat gagcactgct    1380
ttaataggac acttctgaga aattcatcag gctgtgaagc gcgccgtgat gaatatcgaa    1440
cagagtttac cacagctttg cagcgcgttg acttattcat gggtcaattc agcgaagtcc    1500
tcttaacatc tatatccacc ttcattaaag agacctcac catagctaat cttgggacat     1560
cagagggtcg cttcatgcag gttgtggttt ctcgatcagg accatcaacc cctcatgtga    1620
attttctcct ggactcccat ccagtgtctc cagaagtgat tgtggagcat acattaaacc    1680
aaaatggcta cacactggtt atcactggga agaagatcac gaagatcca ttgaatggct     1740
gggctgcag acatttccag tcctgcagtc aatgcctctc tgccccaccc tttgttcagt    1800
gtggctggtg ccacgacaaa tgtgtgcgat cggaggaatg cctgagcggg acatggactc    1860
aacagatctg tctgcctgca atctacaagg ttttcccaaa tagtgcaccc cttgaaggag    1920
ggacaaggct gaccatatgt ggctgggact ttggatttcg gaggaataat aaatttgatt    1980
taaagaaaac tagagttctc cttggaaatg agagctgcac cttgacttta agtgagagca    2040
cgatgaatac attgaaatgc acagttggtc ctgccatgaa taagcatttc aatatgtcca    2100
taattatttc aaatggccac gggacaacac aatacagtac attctcctat gtggatcctg    2160
taataacaag tatttcgccg aaatacggtc ctatggctgg tggcactttta cttactttaa    2220
ctggaaatta cctaaacagt gggaattcta gacacatttc aattggtgga aaaacatgta    2280
```

```
ctttaaaaag tgtgtcaaac agtattcttg aatgttatac cccagcccaa accatttcaa    2340
ctgagtttgc tgttaaattg aaaattgact tagccaaccg agagacaagc atcttcagtt    2400
accgtgaaga tcccattgtc tatgaaattc atccaaccaa atctttattt agtacttggt    2460
ggaaagaacc tctcaacatt gtcagttttc tattttgctt tgccagtggt gggagcacaa    2520
taacaggtgt tgggaaaaac ctgaattcag ttagtgtccc gagaatggtc ataaatgtgc    2580
atgaagcagg aaggaacttt acagtggcat gtcaacatcg ctctaattca gagataatct    2640
gttgtaccac tccttccctg caacagctga atctgcaact cccctgaaa accaaagcct     2700 ttttcatgtt agatgggatc ctttccaaat actttgatct catttatgta cataatcctg    2760
tgtttaagcc ttttgaaaag ccagtgatga tctcaatggg caatgaaaat gtactggaaa    2820
ttaagggaaa tgatattgac cctgaagcag ttaaaggtga agtgttaaaa gttgaaaata    2880
agagctgtga gaatatacac ttacattctg aagccgtttt atgcacggtc cccaatgacc    2940
tgctgaaatt gaacagcgag ctaaatatag agtggaagca agcaatttct tcaaccgtcc    3000
ttggaaaagt aatagttcaa ccagatcaga atttcacagg attgattgct ggtgttgtct    3060
caatatcaac agcactgtta ttactacttg gttttttcct gtggctgaaa aagagaaagc    3120
aaattaaaga tctgggcagt gaattagttc gctacgatgc aagagtacac actcctcatt    3180
tggataggct tgtaagtgcc cgaagtgtaa gcccaactac agaaatggtt tcaaatgaat    3240
ctgtagacta ccgagctact tttccagaag atcagtttcc taattcatct cagaacggtt    3300
catgccgaca agtgcagtat cctctgacag acatgtcccc catcctaact agtggggact    3360
ctgatatatc cagtccatta ctgcaaaata ctgtccacat tgacctcagt gctctaaatc    3420
cagagctggt ccaggcagtg cagcatgtag tgattgggcc cagtagcctg attgtgcatt    3480
tcaatgaagt cataggaaga gggcattttg gttgtgtata tcatgggact tgttggaca    3540 atgatggcaa gaaaattcac tgtgctgtga atcccttgaa cagaatcact gacataggag    3600
aagtttccca atttctgacc gagggaatca tcatgaaaga ttttagtcat cccaatgtcc    3660
tctcgctcct gggaatctgc ctgcgaagtg aagggtctcc gctggtggtc ctaccataca    3720
tgaaacatgg agatcttcga aatttcattc gaaatgagac tcataatcca actgtaaaag    3780
atcttattgg ctttggtctt caagtagcca aagcgatgaa atatcttgca agcaaaaagt    3840
ttgtccacag agacttggct gcaagaaact gtatgctgga tgaaaaattc acagtcaagg    3900
ttgctgattt tggtcttgcc agagacatgt atgataaaga atactatagt gtacacaaca    3960
aaacaggtgc aaagctgcca gtgaagtgga tggctttgga aagtctgcaa actcaaaagt    4020
ttaccaccaa gtcagatgtg tggtcctttg gcgtcgtcct ctgggagctg atgacaagag    4080
gagccccacc ttatcctgac gtaaacacct tgatataac tgtttacttg ttgcaaggga    4140
gaagactcct acaacccgaa tactgcccag accccttata tgaagtaatg ctaaaatgct    4200
ggcaccctaa agccgaaatg cgcccatcct ttctgaact ggtgtcccgg atatcagcga    4260
tcttctctac tttcattggg gagcactatg tccatgtgaa cgctacttat gtgaacgtaa    4320
aatgtgtcgc tccgtatcct tctctgttgt catcagaaga taacgctgat gatgaggtgg    4380
acacacgacc agcctccttc tgggagacat catagtgcta gtactatgtc aaagcaacag    4440
tccacacttt gtccaatggt ttttcactg cctgaccttt aaaaggccat cgatattctt     4500
tgctccttgc cataggactt gtattgttat ttaaattact ggattctaag gaatttctta    4560
tctgacagag catcagaacc agaggcttgg tcccacaggc cagggaccaa tgcgctgcag    4620
```

<210> SEQ ID NO 2
<211> LENGTH: 1408
<212> TYPE: PRT
<213> ORGANISM: Homo sapiens

<400> SEQUENCE: 2

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
225                 230                 235                 240

Phe Arg Asp Ser Tyr Pro Ile Lys Tyr Val His Ala Phe Glu Ser Asn
                245                 250                 255

Asn Phe Ile Tyr Phe Leu Thr Val Gln Arg Glu Thr Leu Asp Ala Gln
            260                 265                 270

Thr Phe His Thr Arg Ile Ile Arg Phe Cys Ser Ile Asn Ser Gly Leu
        275                 280                 285

His Ser Tyr Met Glu Met Pro Leu Glu Cys Ile Leu Thr Glu Lys Arg
    290                 295                 300

Lys Lys Arg Ser Thr Lys Lys Glu Val Phe Asn Ile Leu Gln Ala Ala
305                 310                 315                 320

Tyr Val Ser Lys Pro Gly Ala Gln Leu Ala Arg Gln Ile Gly Ala Ser
                325                 330                 335

Leu Asn Asp Asp Ile Leu Phe Gly Val Phe Ala Gln Ser Lys Pro Asp
            340                 345                 350

Ser Ala Glu Pro Met Asp Arg Ser Ala Met Cys Ala Phe Pro Ile Lys
        355                 360                 365

Tyr Val Asn Asp Phe Phe Asn Lys Ile Val Asn Lys Asn Asn Val Arg
    370                 375                 380
```

```
Cys Leu Gln His Phe Tyr Gly Pro Asn His Glu His Cys Phe Asn Arg
385                 390                 395                 400

Thr Leu Leu Arg Asn Ser Ser Gly Cys Glu Ala Arg Arg Asp Glu Tyr
            405                 410                 415

Arg Thr Glu Phe Thr Thr Ala Leu Gln Arg Val Asp Leu Phe Met Gly
        420                 425                 430

Gln Phe Ser Glu Val Leu Leu Thr Ser Ile Ser Thr Phe Ile Lys Gly
        435                 440                 445

Asp Leu Thr Ile Ala Asn Leu Gly Thr Ser Glu Gly Arg Phe Met Gln
450                 455                 460

Val Val Val Ser Arg Ser Gly Pro Ser Thr Pro His Val Asn Phe Leu
465                 470                 475                 480

Leu Asp Ser His Pro Val Ser Pro Glu Val Ile Val Glu His Thr Leu
            485                 490                 495

Asn Gln Asn Gly Tyr Thr Leu Val Ile Thr Gly Lys Lys Ile Thr Lys
            500                 505                 510

Ile Pro Leu Asn Gly Leu Gly Cys Arg His Phe Gln Ser Cys Ser Gln
            515                 520                 525

Cys Leu Ser Ala Pro Pro Phe Val Gln Cys Gly Trp Cys His Asp Lys
530                 535                 540

Cys Val Arg Ser Glu Glu Cys Leu Ser Gly Thr Trp Thr Gln Gln Ile
545                 550                 555                 560

Cys Leu Pro Ala Ile Tyr Lys Val Phe Pro Asn Ser Ala Pro Leu Glu
                565                 570                 575

Gly Gly Thr Arg Leu Thr Ile Cys Gly Trp Asp Phe Gly Phe Arg Arg
            580                 585                 590

Asn Asn Lys Phe Asp Leu Lys Lys Thr Arg Val Leu Leu Gly Asn Glu
            595                 600                 605

Ser Cys Thr Leu Thr Leu Ser Glu Ser Thr Met Asn Thr Leu Lys Cys
    610                 615                 620

Thr Val Gly Pro Ala Met Asn Lys His Phe Asn Met Ser Ile Ile Ile
625                 630                 635                 640

Ser Asn Gly His Gly Thr Thr Gln Tyr Ser Thr Phe Ser Tyr Val Asp
                645                 650                 655

Pro Val Ile Thr Ser Ile Ser Pro Lys Tyr Gly Pro Met Ala Gly Gly
            660                 665                 670

Thr Leu Leu Thr Leu Thr Gly Asn Tyr Leu Asn Ser Gly Asn Ser Arg
            675                 680                 685

His Ile Ser Ile Gly Gly Lys Thr Cys Thr Leu Lys Ser Val Ser Asn
    690                 695                 700

Ser Ile Leu Glu Cys Tyr Thr Pro Ala Gln Thr Ile Ser Thr Glu Phe
705                 710                 715                 720

Ala Val Lys Leu Lys Ile Asp Leu Ala Asn Arg Glu Thr Ser Ile Phe
                725                 730                 735

Ser Tyr Arg Glu Asp Pro Ile Val Tyr Glu Ile His Pro Thr Lys Ser
            740                 745                 750

Phe Ile Ser Thr Trp Trp Lys Glu Pro Leu Asn Ile Val Ser Phe Leu
            755                 760                 765

Phe Cys Phe Ala Ser Gly Gly Ser Thr Ile Thr Gly Val Gly Lys Asn
            770                 775                 780

Leu Asn Ser Val Ser Val Pro Arg Met Val Ile Asn Val His Glu Ala
785                 790                 795                 800

Gly Arg Asn Phe Thr Val Ala Cys Gln His Arg Ser Asn Ser Glu Ile
```

-continued

```
              805                 810                 815
Ile Cys Cys Thr Thr Pro Ser Leu Gln Gln Leu Asn Leu Gln Leu Pro
        820                 825                 830
Leu Lys Thr Lys Ala Phe Phe Met Leu Asp Gly Ile Leu Ser Lys Tyr
        835                 840                 845
Phe Asp Leu Ile Tyr Val His Asn Pro Val Phe Lys Pro Phe Glu Lys
        850                 855                 860
Pro Val Met Ile Ser Met Gly Asn Glu Asn Val Leu Glu Ile Lys Gly
865                 870                 875                 880
Asn Asp Ile Asp Pro Glu Ala Val Lys Gly Glu Val Leu Lys Val Gly
                885                 890                 895
Asn Lys Ser Cys Glu Asn Ile His Leu His Ser Glu Ala Val Leu Cys
                900                 905                 910
Thr Val Pro Asn Asp Leu Leu Lys Leu Asn Ser Glu Leu Asn Ile Glu
                915                 920                 925
Trp Lys Gln Ala Ile Ser Ser Thr Val Leu Gly Lys Val Ile Val Gln
                930                 935                 940
Pro Asp Gln Asn Phe Thr Gly Leu Ile Ala Gly Val Val Ser Ile Ser
945                 950                 955                 960
Thr Ala Leu Leu Leu Leu Leu Gly Phe Phe Leu Trp Leu Lys Lys Arg
                965                 970                 975
Lys Gln Ile Lys Asp Leu Gly Ser Glu Leu Val Arg Tyr Asp Ala Arg
                980                 985                 990
Val His Thr Pro His Leu Asp Arg  Leu Val Ser Ala Arg  Ser Val Ser
            995                 1000                1005
Pro Thr  Thr Glu Met Val Ser  Asn Glu Ser Val Asp   Tyr Arg Ala
    1010                1015                1020
Thr Phe  Pro Glu Asp Gln Phe  Pro Asn Ser Ser Gln   Asn Gly Ser
    1025                1030                1035
Cys Arg  Gln Val Gln Tyr Pro  Leu Thr Asp Met Ser   Pro Ile Leu
    1040                1045                1050
Thr Ser  Gly Asp Ser Asp Ile  Ser Ser Pro Leu Leu   Gln Asn Thr
    1055                1060                1065
Val His  Ile Asp Leu Ser Ala  Leu Asn Pro Glu Leu   Val Gln Ala
    1070                1075                1080
Val Gln  His Val Val Ile Gly  Pro Ser Ser Leu Ile   Val His Phe
    1085                1090                1095
Asn Glu  Val Ile Gly Arg Gly  His Phe Gly Cys Val   Tyr His Gly
    1100                1105                1110
Thr Leu  Leu Asp Asn Asp Gly  Lys Lys Ile His Cys   Ala Val Lys
    1115                1120                1125
Ser Leu  Asn Arg Ile Thr Asp  Ile Gly Glu Val Ser   Gln Phe Leu
    1130                1135                1140
Thr Glu  Gly Ile Ile Met Lys  Asp Phe Ser His Pro   Asn Val Leu
    1145                1150                1155
Ser Leu  Leu Gly Ile Cys Leu  Arg Ser Glu Gly Ser   Pro Leu Val
    1160                1165                1170
Val Leu  Pro Tyr Met Lys His  Gly Asp Leu Arg Asn   Phe Ile Arg
    1175                1180                1185
Asn Glu  Thr His Asn Pro Thr  Val Lys Asp Leu Ile   Gly Phe Gly
    1190                1195                1200
Leu Gln  Val Ala Lys Ala Met  Lys Tyr Leu Ala Ser   Lys Lys Phe
    1205                1210                1215
```

-continued

```
Val His Arg Asp Leu Ala Ala Arg Asn Cys Met Leu Asp Glu Lys
    1220                1225                1230

Phe Thr Val Lys Val Ala Asp Phe Gly Leu Ala Arg Asp Met Tyr
    1235                1240                1245

Asp Lys Glu Tyr Tyr Ser Val His Asn Lys Thr Gly Ala Lys Leu
    1250                1255                1260

Pro Val Lys Trp Met Ala Leu Glu Ser Leu Gln Thr Gln Lys Phe
    1265                1270                1275

Thr Thr Lys Ser Asp Val Trp Ser Phe Gly Val Val Leu Trp Glu
    1280                1285                1290

Leu Met Thr Arg Gly Ala Pro Pro Tyr Pro Asp Val Asn Thr Phe
    1295                1300                1305

Asp Ile Thr Val Tyr Leu Leu Gln Gly Arg Arg Leu Leu Gln Pro
    1310                1315                1320

Glu Tyr Cys Pro Asp Pro Leu Tyr Glu Val Met Leu Lys Cys Trp
    1325                1330                1335

His Pro Lys Ala Glu Met Arg Pro Ser Phe Ser Glu Leu Val Ser
    1340                1345                1350

Arg Ile Ser Ala Ile Phe Ser Thr Phe Ile Gly Glu His Tyr Val
    1355                1360                1365

His Val Asn Ala Thr Tyr Val Asn Val Lys Cys Val Ala Pro Tyr
    1370                1375                1380

Pro Ser Leu Leu Ser Ser Glu Asp Asn Ala Asp Asp Glu Val Asp
    1385                1390                1395

Thr Arg Pro Ala Ser Phe Trp Glu Thr Ser
    1400                1405

<210> SEQ ID NO 3
<211> LENGTH: 4140
<212> TYPE: DNA
<213> ORGANISM: Mus musculus

<400> SEQUENCE: 3
atgaaggctc ccaccgtgct ggcacctggc attctggtgc tgctgttgtc cttggtgcag      60
aggagccatg gggagtgcaa ggaggcccta gtgaagtctg agatgaacgt gaacatgaag     120
tatcagctcc ccaacttcac ggcagaaacc cccatccaga atgtcgtcct acacggccat     180
catatttatc tcggagccac aaactacatt tatgttttaa atgacaaaga ccttcagaag     240
gtatccgaat tcaagaccgg gcccgtgttg gaacacccag attgtttacc ttgtcgggac     300
tgcagcagca agccaattc atcaggaggg gtttggaaag acaacatcaa catggctctg     360
cttgttgaca catactatga tgatcaactc attagctgtg gcagtgtcaa cagagggact     420
tgccagcggc atgtccttcc tcctgacaat tctgctgaca tccagtctga ggtccactgc     480
atgttctccc cagaagagga gtcagggcag tgtcctgact gtgtagtgag tgccctcgga     540
gccaaagtcc tcctgtcgga aaaggaccgg ttcatcaatt tctttgtggg aatacgatc      600 aattcctcct atcctcctgg ttattcactg cattcgatat cggtgagacg gctgaaggaa     660
acccaagatg gttttaagtt tttgacagac cagtcctata ttgatgtctt accagaattc     720
caagattcct accccataaa gtacatacat gccttcgaaa gcaaccattt tatttacttt     780
ctgactgtcc aaaaggaaac tctagatgct cagactttc atacaagaat aatcaggttc     840
tgttccgtag actctgggtt gcactcctac atggaaatgc cctggaatg catcctgaca     900 gaaaaaagaa ggaagagatc cacaagggaa gaagtgttta atatcctcca agccgcgtat     960
```

```
gtcagtaaac caggggccaa tcttgctaag caaataggag ctagcccttc tgatgacatt    1020
ctcttcgggg tgtttgcaca aagcaagcca gattctgctg aacctgtgaa tcgatcagca    1080
gtctgtgcat tccccatcaa atatgtcaat gacttcttca acaagattgt caacaaaaac    1140
aacgtgagat gtctccagca tttttacgga cccaaccatg agcactgttt caataggacc    1200
ctgctgagaa actcttccgg ctgtgaagcg cgcagtgacg agtatcggac agagtttacc    1260
acggctttgc agcgcgtcga cttattcatg ggccggctta accaagtgct cctgacatcc    1320
atctccacct tcatcaaagg tgacctcacc attgctaatc tagggacgtc agaaggtcgc    1380
ttcatgcagg tggtgctctc tcgaacagca cacctcactc tcatgtgaa cttcctcctg      1440 gactcccatc ctgtatctcc agaagttatt gttgagcatc catcaaatca aaatggctat    1500
acattggttg tcacaggaaa aagatcacc aagattccat gaatggcct gggctgtgga      1560 catttccaat cctgcagtca gtgcctctct gccccttact ttatacagtg tggctggtgc    1620
cacaatcaat gtgtgcgttt tgatgaatgc cccagcggta catggactca agagatctgt    1680
ctgccggcgg tttataaggt gttccccacc agcgcgcccc ttgaaggagg aacagtgttg    1740
accatatgtg gctgggactt tggattcagg aagaataata aatttgattt aaggaaaacc    1800
aaagttctgc ttggcaacga gagctgtacc ttgaccttaa gcgagagcac gacaaatacg    1860
ttgaaatgca cagttggtcc cgcgatgagt gagcacttca atgtgtctgt aattatctca    1920
aacagtcgag agacgacgca atacagtgca ttctcctatg tagatcctgt aataacaagc    1980
atttctccga ggtacggccc tcaggctgga ggcaccttac tcactcttac tgggaaatac    2040
ctcaacagtg gcaattctag acacatttca attggaggga aaacatgtac tttaaaaagt    2100
gtatcagata gtattcttga atgctacacc ccagcccaaa ctacctctga tgagtttcct    2160
gtgaaattga agattgactt ggctaaccga gagaccagca gcttcagtta ccgggaagac    2220
cccgttgtct atgaaatcca cccgaccaaa tcttttatta gtggtggaag cacaataacg    2280
ggtattggga agaccctgaa ctcggttagc ctcccaaagc tggtaataga tgtgcatgaa    2340
gtgggtgtga actacacagt ggcatgtcag catcgctcaa attcagagat catctgctgc    2400
actactcctt cactgaaaca gctgggcctg caactccccc tgaagaccaa agccttcttc    2460
ctgttagacg ggattctttc caaacacttt gatctcactt atgtgcataa tcctgtgttt    2520
gagccttttg aaaagccagt aatgatctca ataggcaatg aaaatgtagt ggaaattaag    2580
ggaaacaata ttgaccctga agcagttaaa ggtgaagtgt taaagttgg aaatcagagc      2640 tgcgagagtc tccactggca ctctggagct gtgttgtgta cagtccccag tgacctgctc    2700
aaactgaaca gcgagctaaa tatagagtgg aagcaagcag tctcttcaac tgttcttgga    2760
aaagtgatcg ttcaaccgga tcagaatttt gcaggattga tcattggtgc ggtctcaata    2820
tcagtagtag ttttgttatt atccgggctc ttcctgtgga tgagaaagag aaagcataaa    2880
gatctgggca gtgaattagt tcgctatgac gcaagagtac acactcctca tttggatagg    2940
cttgtaagtg cccgaagtgt aagtccaact acagagatgg tttcaaatga gtctgtagac    3000
tacagagcta cttttccaga agaccagttt cccaactcct ctcagaatgg agcatgcaga    3060
caagtgcaat accctctgac agacctgtcc cctatcctga caagtggaga ctctgatata    3120
tccagcccat tactacaaaa tactgttcac attgacctca gtgctctaaa tccagagctg    3180
gtccaagcag ttcagcacgt agtgattgga cccagcagcc tgattgtgca tttcaatgaa    3240
gtcataggaa gagggcattt tggctgtgtc tatcatggga ctttgctgga caatgacgga    3300
```

```
aagaaaattc actgtgctgt gaaatcctta aatagaatca cagatataga agaggtctcc  3360
cagtttctga ctgagggaat catcatgaaa gacttcagcc atcccaatgt tctctcactc  3420
ttgggaatct gcctgaggag tgaagggtct cctctggtgg tcctgcccta tatgaagcat  3480
ggagatctgc gaaatttcat tcgaaacgag actcataatc caactgtgaa agatcttata  3540
ggatttggcc ttcaagtagc caaaggcatg aaatatcttg ccagcaaaaa gtttgtccac  3600
agagacttag ctgcaagaaa ctgcatgttg atgaaaaat tcactgtcaa ggttgctgat  3660
ttcggtcttg ccagagacat gtacgataaa gagtactata gtgtccacaa caagacgggt  3720
gccaagctac cagtaaagtg gatggcttta gagagtctgc aaacgcagaa gttcaccacc  3780
aagtcagatg tgtggtcctt tggtgtgctc ctctgggagc tcatgacgag aggagcccct  3840
ccttatcccg acgtgaacac atttgatatc actatctacc tgttgcaagg cagaagactc  3900
ttgcaaccag aatactgtcc agacgccttg tacgaagtga tgctaaaatg ctggcacccc  3960
aaagcggaaa tgcgcccgtc cttttccgaa ctggtctcca ggatatcctc aatcttctcc  4020
acgttcattg gggaacacta cgtccacgtg aacgctactt atgtgaatgt aaaatgtgtt  4080
gctccatatc cttctctgtt gccatcccaa gacaacattg atggcgaggg gaacacatga  4140
```

<210> SEQ ID NO 4
<211> LENGTH: 1379
<212> TYPE: PRT
<213> ORGANISM: Mus musculus

<400> SEQUENCE: 4

| | | | | | | | | | | | | | | |
|---|---|---|---|---|---|---|---|---|---|---|---|---|---|---|
| Met | Lys | Ala | Pro | Thr | Val | Leu | Ala | Pro | Gly | Ile | Leu | Val | Leu | Leu |
| 1 | | | | 5 | | | | | 10 | | | | | 15 |
| Ser | Leu | Val | Gln | Arg | Ser | His | Gly | Glu | Cys | Lys | Glu | Ala | Leu | Lys |
| | | | 20 | | | | | 25 | | | | | 30 | |
| Ser | Glu | Met | Asn | Val | Asn | Met | Lys | Tyr | Gln | Leu | Pro | Asn | Phe | Thr | Ala |
| | | 35 | | | | | 40 | | | | | 45 | | |
| Glu | Thr | Pro | Ile | Gln | Asn | Val | Val | Leu | His | Gly | His | His | Ile | Tyr | Leu |
| | 50 | | | | | 55 | | | | | 60 | | | | |
| Gly | Ala | Thr | Asn | Tyr | Ile | Tyr | Val | Leu | Asn | Asp | Lys | Asp | Leu | Gln | Lys |
| 65 | | | | | 70 | | | | | 75 | | | | | 80 |
| Val | Ser | Glu | Phe | Lys | Thr | Gly | Pro | Val | Leu | Glu | His | Pro | Asp | Cys | Leu |
| | | | | 85 | | | | | 90 | | | | | 95 | |
| Pro | Cys | Arg | Asp | Cys | Ser | Ser | Lys | Ala | Asn | Ser | Ser | Gly | Gly | Val | Trp |
| | | | 100 | | | | | 105 | | | | | 110 | | |
| Lys | Asp | Asn | Ile | Asn | Met | Ala | Leu | Leu | Val | Asp | Thr | Tyr | Tyr | Asp | Asp |
| | | | 115 | | | | | 120 | | | | | 125 | | |
| Gln | Leu | Ile | Ser | Cys | Gly | Ser | Val | Asn | Arg | Gly | Thr | Cys | Gln | Arg | His |
| | 130 | | | | | 135 | | | | | 140 | | | | |
| Val | Leu | Pro | Pro | Asp | Asn | Ser | Ala | Asp | Ile | Gln | Ser | Glu | Val | His | Cys |
| 145 | | | | | 150 | | | | | 155 | | | | | 160 |
| Met | Phe | Ser | Pro | Glu | Glu | Glu | Ser | Gly | Gln | Cys | Pro | Asp | Cys | Val | Val |
| | | | | 165 | | | | | 170 | | | | | 175 | |
| Ser | Ala | Leu | Gly | Ala | Lys | Val | Leu | Leu | Ser | Glu | Lys | Asp | Arg | Phe | Ile |
| | | | 180 | | | | | 185 | | | | | 190 | | |
| Asn | Phe | Phe | Val | Gly | Asn | Thr | Ile | Asn | Ser | Ser | Tyr | Pro | Pro | Gly | Tyr |
| | | | 195 | | | | | 200 | | | | | 205 | | |
| Ser | Leu | His | Ser | Ile | Ser | Val | Arg | Arg | Leu | Lys | Glu | Thr | Gln | Asp | Gly |
| | 210 | | | | | 215 | | | | | 220 | | | | |
| Phe | Lys | Phe | Leu | Thr | Asp | Gln | Ser | Tyr | Ile | Asp | Val | Leu | Pro | Glu | Phe |

```
                225                 230                 235                 240
Gln Asp Ser Tyr Pro Ile Lys Tyr Ile His Ala Phe Glu Ser Asn His
                245                 250                 255
Phe Ile Tyr Phe Leu Thr Val Gln Lys Glu Thr Leu Asp Ala Gln Thr
                260                 265                 270
Phe His Thr Arg Ile Ile Arg Phe Cys Ser Val Asp Ser Gly Leu His
                275                 280                 285
Ser Tyr Met Glu Met Pro Leu Glu Cys Ile Leu Thr Glu Lys Arg Arg
                290                 295                 300
Lys Arg Ser Thr Arg Glu Glu Val Phe Asn Ile Leu Gln Ala Ala Tyr
305                 310                 315                 320
Val Ser Lys Pro Gly Ala Asn Leu Ala Lys Gln Ile Gly Ala Ser Pro
                325                 330                 335
Ser Asp Asp Ile Leu Phe Gly Val Phe Ala Gln Ser Lys Pro Asp Ser
                340                 345                 350
Ala Glu Pro Val Asn Arg Ser Ala Val Cys Ala Phe Pro Ile Lys Tyr
                355                 360                 365
Val Asn Asp Phe Phe Asn Lys Ile Val Asn Lys Asn Asn Val Arg Cys
                370                 375                 380
Leu Gln His Phe Tyr Gly Pro Asn His Glu His Cys Phe Asn Arg Thr
385                 390                 395                 400
Leu Leu Arg Asn Ser Ser Gly Cys Glu Ala Arg Ser Asp Glu Tyr Arg
                405                 410                 415
Thr Glu Phe Thr Thr Ala Leu Gln Arg Val Asp Leu Phe Met Gly Arg
                420                 425                 430
Leu Asn Gln Val Leu Leu Thr Ser Ile Ser Thr Phe Ile Lys Gly Asp
                435                 440                 445
Leu Thr Ile Ala Asn Leu Gly Thr Ser Glu Gly Arg Phe Met Gln Val
                450                 455                 460
Val Leu Ser Arg Thr Ala His Leu Thr Pro His Val Asn Phe Leu Leu
465                 470                 475                 480
Asp Ser His Pro Val Ser Pro Glu Val Ile Val Glu His Pro Ser Asn
                485                 490                 495
Gln Asn Gly Tyr Thr Leu Val Val Thr Gly Lys Lys Ile Thr Lys Ile
                500                 505                 510
Pro Leu Asn Gly Leu Gly Cys Gly His Phe Gln Ser Cys Ser Gln Cys
                515                 520                 525
Leu Ser Ala Pro Tyr Phe Ile Gln Cys Gly Trp Cys His Asn Gln Cys
                530                 535                 540
Val Arg Phe Asp Glu Cys Pro Ser Gly Thr Trp Thr Gln Glu Ile Cys
545                 550                 555                 560
Leu Pro Ala Val Tyr Lys Val Phe Pro Thr Ser Ala Pro Leu Glu Gly
                565                 570                 575
Gly Thr Val Leu Thr Ile Cys Gly Trp Asp Phe Gly Phe Arg Lys Asn
                580                 585                 590
Asn Lys Phe Asp Leu Arg Lys Thr Lys Val Leu Leu Gly Asn Glu Ser
                595                 600                 605
Cys Thr Leu Thr Leu Ser Glu Ser Thr Thr Asn Thr Leu Lys Cys Thr
                610                 615                 620
Val Gly Pro Ala Met Ser Glu His Phe Asn Val Ser Val Ile Ile Ser
625                 630                 635                 640
Asn Ser Arg Glu Thr Thr Gln Tyr Ser Ala Phe Ser Tyr Val Asp Pro
                645                 650                 655
```

-continued

```
Val Ile Thr Ser Ile Ser Pro Arg Tyr Gly Pro Gln Ala Gly Gly Thr
            660                 665                 670

Leu Leu Thr Leu Thr Gly Lys Tyr Leu Asn Ser Gly Asn Ser Arg His
            675                 680                 685

Ile Ser Ile Gly Gly Lys Thr Cys Thr Leu Lys Ser Val Ser Asp Ser
            690                 695                 700

Ile Leu Glu Cys Tyr Thr Pro Ala Gln Thr Thr Ser Asp Glu Phe Pro
705                 710                 715                 720

Val Lys Leu Lys Ile Asp Leu Ala Asn Arg Glu Thr Ser Ser Phe Ser
                725                 730                 735

Tyr Arg Glu Asp Pro Val Val Tyr Glu Ile His Pro Thr Lys Ser Phe
            740                 745                 750

Ile Ser Gly Gly Ser Thr Ile Thr Gly Ile Gly Lys Thr Leu Asn Ser
            755                 760                 765

Val Ser Leu Pro Lys Leu Val Ile Asp Val His Glu Val Gly Val Asn
            770                 775                 780

Tyr Thr Val Ala Cys Gln His Arg Ser Asn Ser Glu Ile Ile Cys Cys
785                 790                 795                 800

Thr Thr Pro Ser Leu Lys Gln Leu Gly Leu Gln Leu Pro Leu Lys Thr
                805                 810                 815

Lys Ala Phe Phe Leu Leu Asp Gly Ile Leu Ser Lys His Phe Asp Leu
            820                 825                 830

Thr Tyr Val His Asn Pro Val Phe Glu Pro Phe Glu Lys Pro Val Met
            835                 840                 845

Ile Ser Ile Gly Asn Glu Asn Val Val Glu Ile Lys Gly Asn Asn Ile
            850                 855                 860

Asp Pro Glu Ala Val Lys Gly Glu Val Leu Lys Val Gly Asn Gln Ser
865                 870                 875                 880

Cys Glu Ser Leu His Trp His Ser Gly Ala Val Leu Cys Thr Val Pro
                885                 890                 895

Ser Asp Leu Leu Lys Leu Asn Ser Glu Leu Asn Ile Glu Trp Lys Gln
            900                 905                 910

Ala Val Ser Ser Thr Val Leu Gly Lys Val Ile Val Gln Pro Asp Gln
            915                 920                 925

Asn Phe Ala Gly Leu Ile Ile Gly Ala Val Ser Ile Ser Val Val Val
            930                 935                 940

Leu Leu Leu Ser Gly Leu Phe Leu Trp Met Arg Lys Arg Lys His Lys
945                 950                 955                 960

Asp Leu Gly Ser Glu Leu Val Arg Tyr Asp Ala Arg Val His Thr Pro
            965                 970                 975

His Leu Asp Arg Leu Val Ser Ala Arg Ser Val Ser Pro Thr Thr Glu
            980                 985                 990

Met Val Ser Asn Glu Ser Val Asp Tyr Arg Ala Thr Phe Pro Glu Asp
            995                 1000                1005

Gln Phe Pro Asn Ser Ser Gln Asn Gly Ala Cys Arg Gln Val Gln
    1010                1015                1020

Tyr Pro Leu Thr Asp Leu Ser Pro Ile Leu Thr Ser Gly Asp Ser
    1025                1030                1035

Asp Ile Ser Ser Pro Leu Leu Gln Asn Thr Val His Ile Asp Leu
    1040                1045                1050

Ser Ala Leu Asn Pro Glu Leu Val Gln Ala Val Gln His Val Val
    1055                1060                1065
```

```
Ile Gly Pro Ser Ser Leu Ile Val His Phe Asn Glu Val Ile Gly
    1070                1075                1080

Arg Gly His Phe Gly Cys Val Tyr His Gly Thr Leu Leu Asp Asn
    1085                1090                1095

Asp Gly Lys Lys Ile His Cys Ala Val Lys Ser Leu Asn Arg Ile
    1100                1105                1110

Thr Asp Ile Glu Glu Val Ser Gln Phe Leu Thr Glu Gly Ile Ile
    1115                1120                1125

Met Lys Asp Phe Ser His Pro Asn Val Leu Ser Leu Leu Gly Ile
    1130                1135                1140

Cys Leu Arg Ser Glu Gly Ser Pro Leu Val Val Leu Pro Tyr Met
    1145                1150                1155

Lys His Gly Asp Leu Arg Asn Phe Ile Arg Asn Glu Thr His Asn
    1160                1165                1170

Pro Thr Val Lys Asp Leu Ile Gly Phe Gly Leu Gln Val Ala Lys
    1175                1180                1185

Gly Met Lys Tyr Leu Ala Ser Lys Lys Phe Val His Arg Asp Leu
    1190                1195                1200

Ala Ala Arg Asn Cys Met Leu Asp Glu Lys Phe Thr Val Lys Val
    1205                1210                1215

Ala Asp Phe Gly Leu Ala Arg Asp Met Tyr Asp Lys Glu Tyr Tyr
    1220                1225                1230

Ser Val His Asn Lys Thr Gly Ala Lys Leu Pro Val Lys Trp Met
    1235                1240                1245

Ala Leu Glu Ser Leu Gln Thr Gln Lys Phe Thr Thr Lys Ser Asp
    1250                1255                1260

Val Trp Ser Phe Gly Val Leu Leu Trp Glu Leu Met Thr Arg Gly
    1265                1270                1275

Ala Pro Pro Tyr Pro Asp Val Asn Thr Phe Asp Ile Thr Ile Tyr
    1280                1285                1290

Leu Leu Gln Gly Arg Arg Leu Leu Gln Pro Glu Tyr Cys Pro Asp
    1295                1300                1305

Ala Leu Tyr Glu Val Met Leu Lys Cys Trp His Pro Lys Ala Glu
    1310                1315                1320

Met Arg Pro Ser Phe Ser Glu Leu Val Ser Arg Ile Ser Ser Ile
    1325                1330                1335

Phe Ser Thr Phe Ile Gly Glu His Tyr Val His Val Asn Ala Thr
    1340                1345                1350

Tyr Val Asn Val Lys Cys Val Ala Pro Tyr Pro Ser Leu Leu Pro
    1355                1360                1365

Ser Gln Asp Asn Ile Asp Gly Glu Gly Asn Thr
    1370                1375

<210> SEQ ID NO 5
<211> LENGTH: 21
<212> TYPE: DNA
<213> ORGANISM: Artificial Sequence
<220> FEATURE:
<223> OTHER INFORMATION: primer for c-met

<400> SEQUENCE: 5
agccagtaat gatctcaata g                                           21

<210> SEQ ID NO 6
<211> LENGTH: 18
<212> TYPE: DNA
```

```
<213> ORGANISM: Artificial Sequence
<220> FEATURE:
<223> OTHER INFORMATION: primer for c-met

<400> SEQUENCE: 6
tcaggatagg ggacaggt                                                  18

<210> SEQ ID NO 7
<211> LENGTH: 23
<212> TYPE: DNA
<213> ORGANISM: Artificial Sequence
<220> FEATURE:
<223> OTHER INFORMATION: primer for beta-actin

<400> SEQUENCE: 7
cgtgacatca aagagaagct gtg                                            23

<210> SEQ ID NO 8
<211> LENGTH: 24
<212> TYPE: DNA
<213> ORGANISM: Artificial Sequence
<220> FEATURE:
<223> OTHER INFORMATION: primer for beta-actin

<400> SEQUENCE: 8
gctcaggagg agcaatgatc ttga                                           24

<210> SEQ ID NO 9
<211> LENGTH: 19
<212> TYPE: DNA
<213> ORGANISM: mus musculus

<400> SEQUENCE: 9
gccgcgtatg tcagtaaac                                                 19

<210> SEQ ID NO 10
<211> LENGTH: 19
<212> TYPE: DNA
<213> ORGANISM: mus musculus

<400> SEQUENCE: 10
gcaaatagga gctagccct                                                 19

<210> SEQ ID NO 11
<211> LENGTH: 19
<212> TYPE: DNA
<213> ORGANISM: mus musculus

<400> SEQUENCE: 11
gcgagagcac gacaaatac                                                 19

<210> SEQ ID NO 12
<211> LENGTH: 19
<212> TYPE: DNA
<213> ORGANISM: mus musculus

<400> SEQUENCE: 12
gtgatcgttc aaccggatc                                                 19

<210> SEQ ID NO 13
<211> LENGTH: 19
<212> TYPE: DNA
<213> ORGANISM: Homo sapiens

<400> SEQUENCE: 13
```

```
gaccttcaga aggttgctg                                                  19

<210> SEQ ID NO 14
<211> LENGTH: 19
<212> TYPE: DNA
<213> ORGANISM: Homo sapiens

<400> SEQUENCE: 14
gccagattct gccgaacca                                                  19

<210> SEQ ID NO 15
<211> LENGTH: 19
<212> TYPE: DNA
<213> ORGANISM: Homo sapiens

<400> SEQUENCE: 15
gtgcagtatc ctctgacag                                                  19

<210> SEQ ID NO 16
<211> LENGTH: 19
<212> TYPE: DNA
<213> ORGANISM: canis familiaris

<400> SEQUENCE: 16
gtgagagcac aacaaatat                                                  19

<210> SEQ ID NO 17
<211> LENGTH: 19
<212> TYPE: DNA
<213> ORGANISM: canis familiaris

<400> SEQUENCE: 17
gtaatagttc aaccagatc                                                  19

<210> SEQ ID NO 18
<211> LENGTH: 19
<212> TYPE: DNA
<213> ORGANISM: Canis familiaris

<400> SEQUENCE: 18
gtacaatatc ctctgacgg                                                  19
```